United States Patent [19]

Foltz et al.

[11] Patent Number: 5,223,401
[45] Date of Patent: Jun. 29, 1993

[54] RAPID READ-OUT STERILITY INDICATOR

[75] Inventors: William E. Foltz, Cottage Grove; Richard R. Matner, St. Paul; Lewis P. Woodson, Eagan, all of Minn.

[73] Assignee: Minnesota Mining and Manufacturing Company, St. Paul, Minn.

[ * ] Notice: The portion of the term of this patent subsequent to Dec. 17, 2008, has been disclaimed.

[21] Appl. No.: 277,570

[22] Filed: Nov. 29, 1988

[51] Int. Cl.$^5$ .......................... C12Q 1/22; C12M 1/12; C12M 1/34; C12M 1/40

[52] U.S. Cl. .......................................... 435/18; 435/4; 435/288; 435/291; 435/295; 435/808; 435/810; 435/31; 435/19; 435/21; 435/23; 435/24; 422/55; 422/56; 422/58; 422/60; 422/61; 422/83; 422/86; 422/101; 436/501; 436/805; 935/38; 935/60; 935/76

[58] Field of Search .................. 435/4, 31, 808, 810, 435/295, 288, 291, 18, 19, 21, 23, 24; 436/501, 805; 935/38, 60, 76; 422/55, 56, 58, 60, 61, 83, 86, 101

[56] References Cited

U.S. PATENT DOCUMENTS

| | | | |
|---|---|---|---|
| 2,854,384 | 9/1958 | Beakley et al. | 195/54 |
| 3,239,429 | 3/1966 | Menolasino et al. | 195/54 |
| 3,346,464 | 10/1967 | Ernst | 195/64 |
| 3,440,144 | 4/1969 | Andersen | 195/103.5 |
| 3,551,295 | 12/1970 | Dyer | 195/103.5 |
| 3,585,112 | 6/1971 | Ernst | 195/103.5 |
| 3,661,717 | 5/1972 | Nelson | 195/103.5 R |
| 3,752,743 | 8/1973 | Henshilwood | 195/127 |
| 3,796,635 | 3/1974 | Delemte | 195/65 |
| 3,846,242 | 11/1974 | Ernst | 195/103.5 |
| 4,011,139 | 3/1977 | Horwath et al. | 195/65 |
| 4,162,942 | 7/1979 | Gunther | 435/17 |
| 4,284,719 | 8/1981 | Agerhem et al. | 435/18 |
| 4,291,122 | 9/1981 | Orelski | 435/31 |
| 4,304,869 | 12/1981 | Dyke | 435/296 |
| 4,416,984 | 11/1983 | Wheeler, Jr. | 435/31 |
| 4,461,837 | 7/1984 | Karle et al. | 435/296 |
| 4,528,268 | 7/1985 | Andersen et al. | 435/31 |
| 4,579,823 | 4/1986 | Ryder | 435/296 |
| 4,580,682 | 4/1986 | Gorski et al. | 206/569 |
| 4,591,554 | 5/1986 | Koumura et al. | 435/18 |
| 4,596,773 | 6/1986 | Wheeler, Jr. | 435/31 |
| 4,603,108 | 7/1986 | Bascomb | 435/34 |
| 4,717,661 | 1/1988 | McCormick et al. | 435/31 |
| 4,743,537 | 5/1988 | McCormick et al. | 435/296 |
| 4,883,641 | 11/1989 | Wicks et al. | 422/50 |

FOREIGN PATENT DOCUMENTS

| | | |
|---|---|---|
| 0000063 | 12/1978 | European Pat. Off. . |
| WO86/05206 | 9/1986 | PCT Int'l Appl. . |
| 1547747 | 6/1979 | United Kingdom . |
| 2128204 | 4/1984 | United Kingdom . |

OTHER PUBLICATIONS

Laurence, D. J. R., "Fluorescence Techniques for the Enzymologist", *Methods in Enzymology*, vol. IV, pp. 174-212 (1957).

Campbell, L. L. Jr., "Purification and Properties of an α-Amylase from Facultative Thermophilic Bacteria", *Archives of Biochemistry and Biophysics*, vol. 54(1), pp. 154-161 (1955).

(List continued on next page.)

*Primary Examiner*—Margaret Moskowitz
*Assistant Examiner*—Ardin H. Marschel
*Attorney, Agent, or Firm*—Gary L. Griswold; Walter N. Kirn; Jennie G. Boeder

[57] ABSTRACT

A unitary sterility indicator and a method for its use, the indicator comprising an outer container having liquid impermeable and gas non-absorptive walls, and having a gas-transmissive, bacteria impermeable opening therein; contained within the outer container, a detectable amount of a source of active enzyme and/or another microorganism commonly used to monitor sterilization; a sealed, openable gas and liquid impermeable inner container containing an aqueous medium and/or a nutrient growth medium, disposed in the outer container; an enzyme substrate system capable of reacting with active enzyme to produce a detectable enzyme-modified product and/or a detector material sensitive to microorganism growth, contained in one of the containers; and means contained within the outer container for restricting the area in which enzyme-modified product and/or growing microorganisms are contained, after the inner container is opened, to an area which is less than the volume of aqueous solution contained in the inner container.

13 Claims, 2 Drawing Sheets

OTHER PUBLICATIONS

Roth, M., "Fluorimetric Assay of Enzymes", *Methods of Biochemical Anaylsis*, vol. 17, pp. 189-285 (1969).

Udenfriend, S., "Fluorescence in Enzymology", *Fluorescence Assay in Biology and Medicine*, Academic Press, New York, pp. 312-348 (1962).

Snyder, A. P. et al., "Pattern Recognition Analysis of In Vivo Enzyme-Substrate Fluorescence Velocities in Microorganism Detection and Identification", *Appl. Environ. Microbiol.*, vol. 51, No. 5, pp. 969-977 (1986).

Warth, A. D., "Heat Stability of *Bacillus cereus* Enzymes Within Spores and in Extracts", *Journal of Bacteriology*, vol. 143, No. 1, pp. 27-34 (1980).

Yutani, K. et al., "Comparison of thermostable α-Amylases from *B. stearothermophilus* Grown at Different Temperatures", *J. Biochem.*, 74, pp. 573-579 (1973).

Suzuki, Y. et al., "Assignment of A ρ-Nitrophenyl α-D-Glucopyranosidase of Bacillus Stearothermophilus ATCC 12016 to A Novel Exo-α-1,4-Glucosidase Active For Oligomaltosaccharides and α-Glucans", *Biochemica et Biophysica Acta.*, 787 pp. 281-289 (1984).

Suzuki, Y. et al., "Production of Extracellular α-Glucosidase by A Thermophilic Bacillus Species", *Applied and Environmental Microbiology*, pp. 807-812 (1976).

Suzuki, Y. et al., "Purification and properties of Extracellular α-Glucosidase of A Thermophile, Bacillus Thermoglucosidius KP 1006", *Biochimica et Biophysica Acta.*, 445, pp. 386-397 (1976).

Suzuki, Y. et al., "Assignment of A ρ-Nitrophenyl-α-D-Glucopyranoside-Hydrolyzing α-Glucosidase of Bacillus Stearothermophilus ATCC 12016 to An Exo-Oligo-1,6-Glucosidase", *Biochemica et Biophysica Acta.*, 704, pp. 476-483 (1982).

Warth, A. D., "Stabilization of Spore Enzymes to Heat by Reduction in Water Activity", *Sporulation and Germination*, Proceedings of the Eighth International Spore Conference, Woods Hole, Mass., pp. 249-252 (1980).

Priest, F. G., "Extracellular Enzyme Synthesis in the Genus Bacillus", *Bacteriological Reviews*, pp. 711-753 (1977).

Hodges, N. A., "A Comparison of Heat Resistance in Commercially Available Bacillus stearothermophilus Spore Preparations Used For Monitoring Steam Sterilization", *J. Phram. Pharmacol.*, 34, 259-260 (1982).

Starkey, D. H., "The Use of Indicators for Quality Control of Sterilizing Processes in Hospital Practice: A Review", *American Journal of Infection Control*, vol. 8, No. 3, pp. 79-84 (1980).

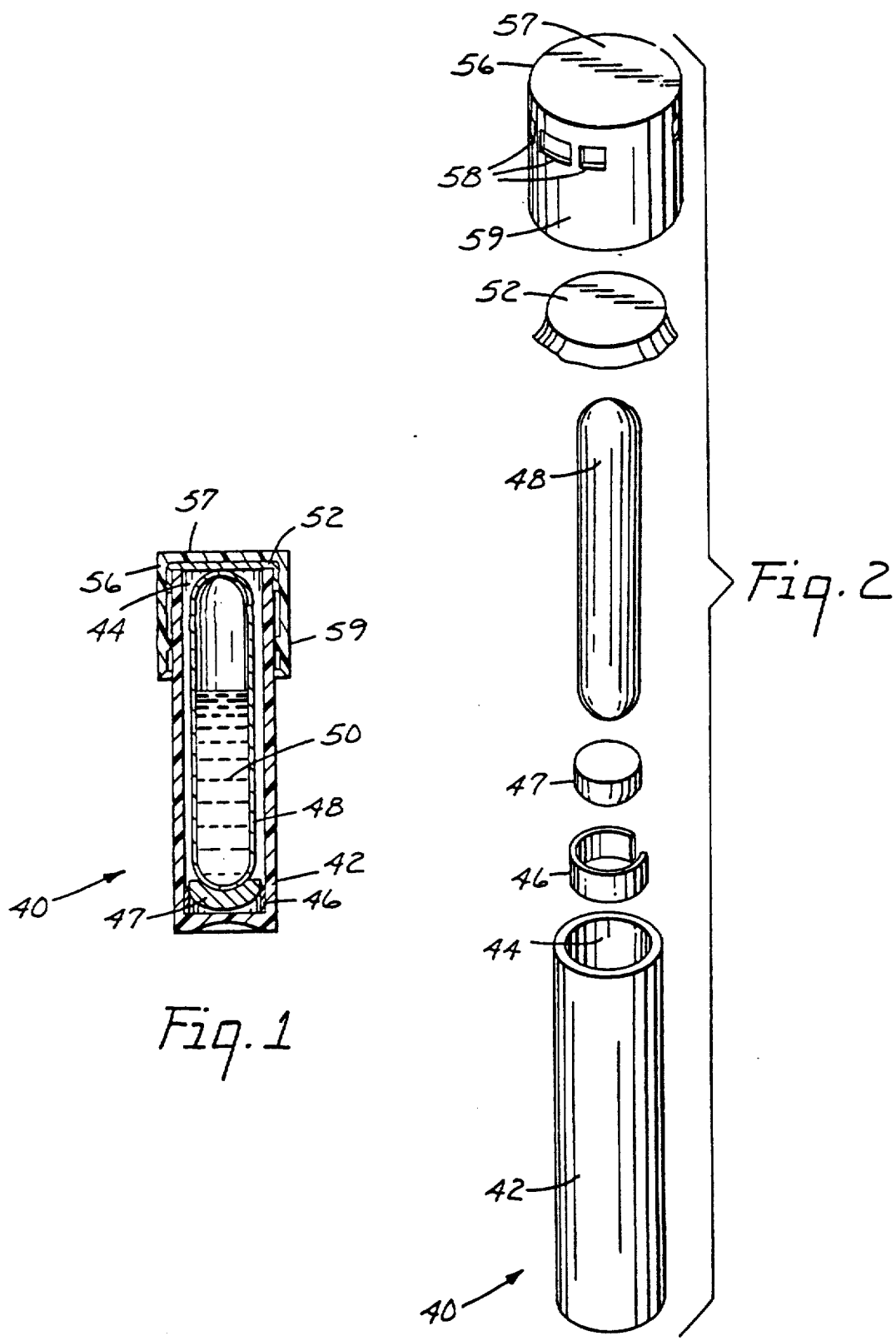

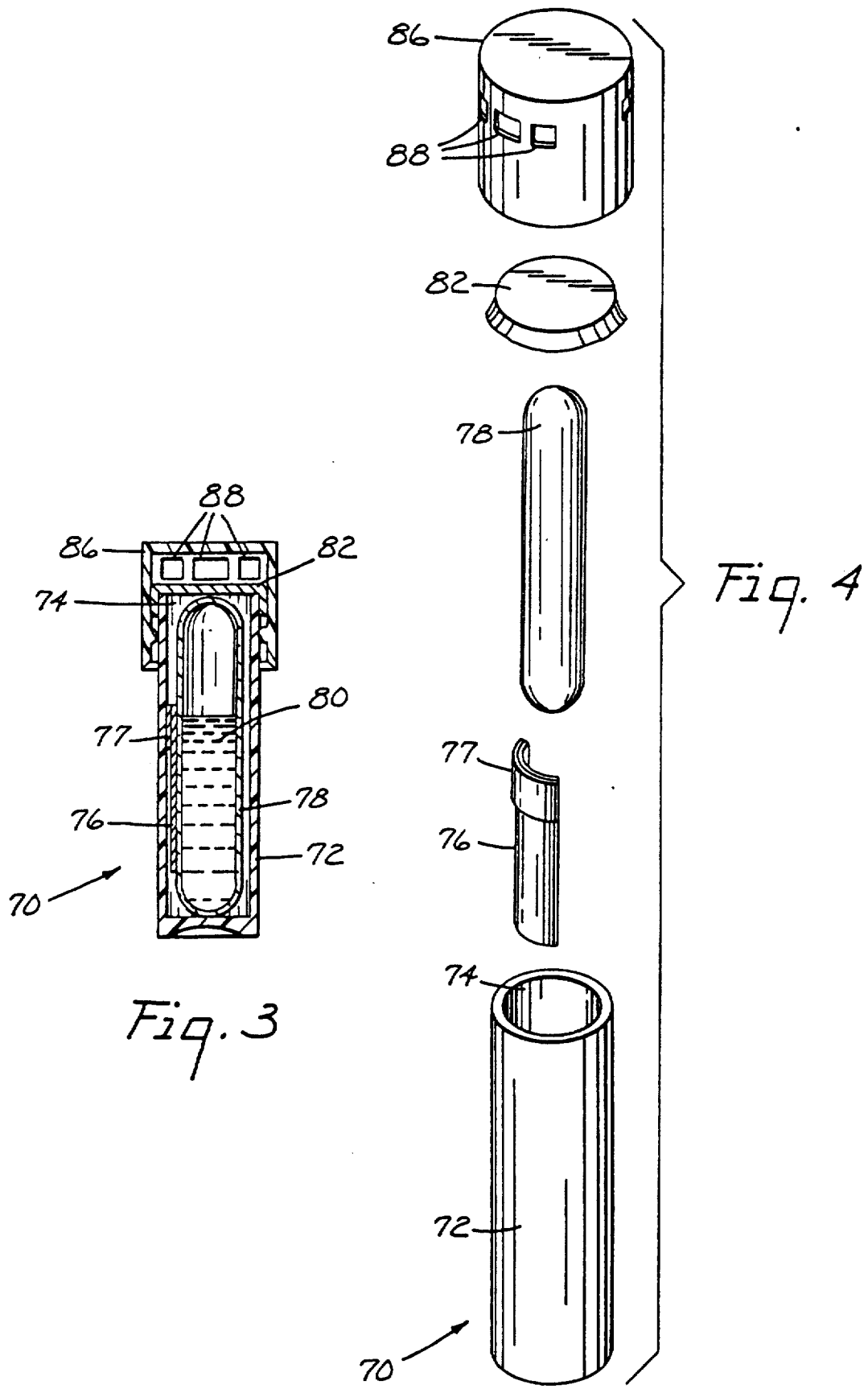

5,223,401

RAPID READ-OUT STERILITY INDICATOR

FIELD OF THE INVENTION

This invention relates to a unitary sterility indicator for determining the efficacy of a sterilization cycle. In particular, the present invention relates to a biological sterility indicator which, due to its construction, enables a more rapid determination of sterilization efficacy. The present invention can provide information on sterilization efficacy within less than twenty-four hours, and, in preferred embodiments, within ten minutes of incubation.

BACKGROUND OF THE INVENTION

Biological indicators and chemical indicators used to determine the efficacy of sterilization are well known in the art. It is well recognized in the art of sterilization that biological tests are the most accurate sterility tests because they provide a high level of confidence that all parameters necessary to achieve sterilization, including the interrelated parameters of time, temperature and concentrations of moisture, chemicals or radiation dose, have been reached. In conventional biological indicators, a test organism which is many times more resistant to the sterilization process employed than most organisms which would be present by natural contamination, is coated on a carrier and placed in a sterilizer along with the articles to be sterilized. After completion of the sterilization cycle, the carrier is incubated in nutrient growth medium to determine whether any of the test organism survived the sterilization procedure.

Several unitary biological indicators, i.e., indicators containing both the test microorganism and the nutrient growth medium, are described in U.S. Pat. Nos. 3,239,429; 3,440,144; 3,661,717; 4,291,122; 4,304,869; 4,416,984; 4,461,837; 4,528,268; 4,579,823; 4,580,682; 4,596,773; and 4,717,661. The sterility indicator described in U.S. Pat. No. 3,661,717, for example, is comprised of a container for a test spore strip with an opening at one end. Also in the container is an ampoule filled with an aqueous nutrient and indicator system. The container is covered with a gas transmissive, bacterial impermeable closure. In use this indicator is placed within the sterilization chamber during the cycle and sterilant enters the container displacing air in the container. Circulation of the sterilant around the spore strip kills the spores. Thereafter the ampoule containing the nutrient and indicator media is crushed upon deformation of the outer compartment and any spores remaining viable are allowed to grow in the nutrient medium. In all of the previously described conventional biological indicators the entire volume of growth medium is observed for indication of spore survival, and growth of a detectable number of microorganisms takes a minimum of twenty-four hours. During this period, the supposedly sterilized articles should be quarantined.

In frequent practice, however, the hospital has neither the space for proper quarantining of the supposedly sterilized articles, nor a sufficient number of the articles themselves to permit actual quarantining. As a result, the supposedly sterilized articles are placed back into stock on the assumption that sterilization was proper and will be confirmed by a subsequent report from the laboratory. Applicants' commonly assigned U.S. Patent entitled "Rapid Method for Determining Efficacy of a Sterilization Cycle and Rapid Read-Out Biological Indicator", (U.S. Pat. No. 5,073,488), filed of even date herewith, describes a method of determining sterilization efficacy which employs an enzyme whose activity can be correlated with the viability of at least one microorganism commonly used to monitor sterilization efficacy. The enzyme, following a sterilization cycle which is sublethal to the test microorganism, remains sufficiently active to react with an enzyme substrate in a relatively short period of time, e.g., normally eight hours or less. However, the enzyme is inactivated or appreciably reduced in activity following a sterilization cycle which is lethal to the test microorganism.

There remains a need for a biological sterility indicator which will provide even more rapid and reliable results.

SUMMARY OF THE INVENTION

The present invention provides devices and methods for indicating sterilization efficacy which can indicate sterilization failure within less than twenty-four hours, and in preferred cases, in less than 8 hours. In a particularly preferred embodiment of the present invention, sterilization failure can be detected within about ten minutes.

In one embodiment the present invention provides a unitary sterility indicator comprising:

a) an outer container having liquid impermeable and substantially gas non-absorptive walls, and having at least one opening therein;

b) a gas-transmissive, bacteria-impermeable means covering said at least one opening;

c) contained within the outer container, a detectable amount of at least one microorganism commonly used to monitor sterilization;

d) a sealed, openable, gas and liquid impermeable inner container, containing an aqueous nutrient medium capable, with incubation, of promoting growth of viable microorganisms, the inner container being disposed in the outer container and the inner container, when opened, permitting the nutrient medium to contact the microorganisms;

e) a detector material contained in at least one of the containers and capable of undergoing a visible color change in response to growth of microorganisms; and f) means contained within, the outer container for restricting the volume of nutrient medium in which the microorganism is allowed to grow, after the inner container is opened and the nutrient medium is allowed to contact the microorganisms, to a volume which is less than the volume of the nutrient medium.

In a preferred embodiment of the present invention there is provided a unitary sterility indicator comprising:

a) an outer container having liquid impermeable and substantially gas non-absorptive walls, and having at least one opening therein;

b) a gas-transmissive, bacteria-impermeable means covering said at least one opening;

c) contained within the outer container a source of active enzyme which provides a detectable amount of an enzyme which has activity which correlates with the viability of at least one microorganism commonly used to monitor sterilization;

d) a sealed, openable gas and liquid impermeable inner container containing an aqueous reaction medium capable of permitting reaction between the active enzyme and a substrate for that enzyme, the inner container being disposed in the outer container and the inner container, when opened, permitting the aqueous reaction medium to contact the source of active enzyme;

e) an enzyme substrate system contained in at least one of the containers, which is capable of reacting in the presence of the aqueous reaction medium with active enzyme to produce a detectable enzyme-modified product; and f) means contained within the outer container for restricting the volume in which the enzyme-modified product is contained, after the inner container is opened and the medium is allowed to contact the source of active enzyme, to a volume which is less than the volume of said aqueous reaction medium contained in said inner container.

The ability of the indicators of the present invention to provide rapid results is due to the presence of the means restricting the volume where the microorganisms may grow, or the enzyme may react with its substrate. Less incubation time is required to detect the growth of microorganisms, or the presence of detectable enzyme-modified product, if the volume in which growth or reaction occurs is restricted to less than the entire volume of the growth medium or reaction mixture. Preferably the volume in which growth or reaction occurs is restricted to less than one-half the volume of the growth medium and/or enzyme substrate system contained in the inner container, and more preferably the volume is restricted to less than one-fourth the volume of the aqueous solution contained in the inner container.

BRIEF DESCRIPTION OF THE FIGURES

FIG. 1 is a cross-sectional view of a preferred embodiment of an indicator of the present invention, with closure 56 in the closed position.

FIG. 2 is an exploded perspective view of the indicator of FIG. 1.

FIG. 3 is a cross-sectional view of another preferred embodiment of a sterility indicator of the present invention, with closure 86 in the open position.

FIG. 4 is an exploded perspective view of the sterility indicator of FIG. 3.

DETAILED DESCRIPTION OF THE INVENTION

Microorganisms which may be employed in the present invention are those conventionally used microorganisms which are generally many times more resistant to the sterilization process being employed than most organisms encountered in natural contamination. Favorable results have been obtained with bacteria and fungi, which exist in both "spore" and "vegetative" states. The bacterial spore is recognized as the most resistant form of microbial life. It is the life form of choice in all tests for determining the sterilizing efficacy of devices, chemicals and processes. Spores from Bacillus and Clostridia species are the most commonly used to monitor sterilization processes utilizing saturated steam, dry heat, gamma irradiation and ethylene oxide.

Particularly preferred microorganisms commonly used to monitor sterilization conditions include *Bacillus stearothermophilus*, *Bacillus subtilis*, and *Bacillus pumilus*. *Bacillus stearothermophilus* is particularly useful to monitor sterilization under steam sterilization conditions. *Bacillus subtilis* is particularly useful to monitor conditions of gas and dry heat sterilization. *Bacillus pumilus* is particularly useful to monitor gamma irradiation sterilization.

In a preferred embodiment of the present invention, the unitary sterility indicator includes a source of active enzyme contained in the outer container, and a substrate system for that enzyme in the inner or outer container. The enzyme substrate system is capable of reacting in the presence of an aqueous reaction medium with active enzyme to produce a detectable enzyme-modified product.

The enzymes useful in the preferred embodiment are enzymes including extracellular and intracellular enzymes, whose activity correlates with the viability of at least one microorganism commonly used to monitor sterilization efficacy, hereinafter referred to as a "test" microorganism. By "correlates" it is meant that the enzyme activity, over background, can be used to predict future growth of the test microorganism. The enzyme must be one which following a sterilization cycle which is sublethal to the test microorganism, remains sufficiently active to react with a substrate system for the enzyme, within twenty-four hours, and in preferred embodiment within eight hours or less, yet be inactivated or appreciably reduced in activity following a sterilization cycle which would be lethal to the test microorganism.

The use of such enzymes to monitor sterilization efficacy is described in Applicants commonly assigned U.S. Patent entitled "Rapid Method for Determining Efficacy of a Sterilization Cycle and Rapid Read-Out Biological Indicator" (U.S. Pat. No. 5,073,488), filed of even date herewith. The method comprises:

a) subjecting to a sterilization cycle a source of active enzyme, said enzyme having activity which correlates with the viability of at least one microorganism commonly used to monitor sterilization; and b) incubating the enzyme source, following the completion of the sterilization cycle, with an effective amount of a substrate system for that enzyme, which system is capable of reacting with any residual active enzyme to produce a detectable enzyme-modified product.

The reaction mixture is then evaluated in, e.g., a fluorometer or a colorimeter, to determine the presence of any enzyme-modified product. Generally applicable methods for detecting enzyme modified product that may be used in biochemical analysis include photometric, potentiometric, gravimetric, calorimetric, conductometric, and amperometric techniques. For the purpose of this invention, fluorometric and spectrophotometric methods of measuring detectable enzyme modified product are preferred. The existence of detectable enzyme-modified product above background within an established period of time (dependent upon the identity of the enzyme and the substrate, the concentration of each, and the incubation conditions) indicates a sterilization failure. The lack of detectable enzyme-modified product within the established period of time indicates a sterilization cycle which would have been lethal to the test organism and is therefor adequate.

The following test has proven useful in identifying those enzymes having the requisite characteristics to be useful in the sterilization monitoring devices of the present invention. The enzyme when subjected to sterilization conditions which would be just sufficient to decrease the population of $1 \times 10^6$ test microorganisms by about 6 logs (i.e., to a population of about zero as measured by outgrowth of the test microorganisms), has residual enzyme activity which is equal to "background" as measured by reaction with a substrate system for the enzyme; however, the enzyme upon being subjected to sterilization conditions sufficient only to decrease the population of $1 \times 10^6$ test microorganisms by at least 1 log, but less than 6 logs, has enzyme activity greater than "background" as measured by reaction with the enzyme substrate system. The enzyme substrate system is a substance, or mixture of substances, which is acted upon by the enzyme to produce a detectable, e.g., luminescent, fluorescent or colored, enzyme-modified product. The enzyme activity is measured by the amount of detectable enzyme-modified product produced. Preferably, the enzyme is one which has sufficient activity, following sterilization conditions insufficient to decrease the population of the test microorganism by 6 logs, to react with the enzyme substrate system and produce a detectable amount of enzyme-modified product within twenty-four hours, preferably within eight or less hours, and most preferably within two or less hours.

Preferably, the activity of the enzyme after sterilization conditions insufficient to decrease the microorganism population by 6 logs, is at least 2 percent greater, and more preferably at least 5 percent greater, than background, and most preferably is at least 10 percent above background. It is understood that the residual enzyme activity level which is defined as "background" for purposes of this invention, may be higher than that achieved by the spontaneous conversion of enzyme substrate to product after the enzyme has been totally and irreversibly inactivated.

Enzymes which have been found to meet the above-described test include hydrolytic enzymes from spore-forming microorganisms. Such enzymes include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, alpha-L-arabinofuranosidase, N-acetyl-$\beta$-glucosaminidase, beta-D-cellobiosidase, alanine aminopeptidase, proline aminopeptidase, tyrosine aminopeptidase, phenylalanine aminopeptidase, beta-D-glucuronidase, and fatty acid esterase derived from spore-forming microorganisms, such as Candida, Bacillus and Clostridium species of microorganisms.

Particularly useful enzymes from *Bacillus stearothermophilus* include alpha-D-glucosidase, beta-D-glucosidase, alkaline phosphatase, acid phosphatase, butyrate esterase, caprylate esterase lipase, leucine aminopeptidase, chymotrypsin, phosphohydrolase, alpha-D-galactosidase, beta-D-galactosidase, alanine aminopeptidase, tyrosine aminopeptidase, phenylalanine aminopeptidase, and a fatty acid esterase. Particularly useful enzymes from *Bacillus subtilis* include alpha-L-arabinofuranosidase, beta-D-glucosidase, N-acetyl-$\beta$-glucosaminidase, beta-D-cellobiosidase, alanine aminopeptidase, proline aminopeptidase, tyrosine aminopeptidase, leucine aminopeptidase, and phenylalanine aminopeptidase.

Beta-D-glucosidase and alpha-L-arabinofuranosidase from *Bacillus subtilis* are particularly useful in the monitoring of ethylene oxide sterilization. Alpha-D-glucosidase from *Bacillus stearothermophilus* is particularly useful to monitor steam sterilization conditions.

The source of active enzyme may be:

1) the purified, isolated enzyme derived from an appropriate microorganism;

2) a microorganism to which the enzyme is indigenous or added by genetic engineering; or 3) a microorganism to which the enzyme has been added during sporulation or growth, such that the enzyme is incorporated or associated with the microorganism, e.g., an enzyme added to a spore during sporulation which becomes incorporated within the spore. Preferred microorganisms which may be utilized as the source of an enzyme useful in the practice of the present invention are bacteria and fungi, in either the spore or vegetative state. Particularly preferred sources of enzyme include Bacillus, Clostridium, Neurospora, and Candida species of microorganisms.

Advantageously, a microorganism which is itself one conventionally used to monitor sterilization conditions, is utilized as the source of active enzyme. Any of the microorganism which remains viable, following the completion of the sterilization cycle, is incubated with nutrient growth medium to confirm by conventional technique whether the sterilization conditions had been sufficient to kill all of the microorganisms in the indicator, indicating that the sterilization conditions had been sufficient to sterilize all of the items in the sterilizer.

Alternatively, in the event that isolated enzyme is utilized, or the microorganism used as the source of the enzyme is not more resistant to the sterilization conditions than the natural contaminants, another microorganism commonly used to monitor sterilization conditions can be exposed to the sterilization cycle along with the enzyme source. Again, in such a case, any viable microorganism remaining after the sterilization cycle, is incubated with an aqueous nutrient medium to confirm the sterilization efficacy.

The present invention, although herein described primarily in terms of a single enzyme and/or microorganism species, should be understood to refer as well to the use of a plurality of enzymes and/or microorganism species. For example, a single sterility indicator may contain three types of isolated enzymes (which may be derived from three types of microorganisms), one enzyme being resistant to heat, a second being resistant to gaseous sterilizing media, and a third being resistant to radiation, e.g., gamma and beta irradiation. Similarly, a single sterility indicator may contain three species of microorganisms, one species being resistant to heat, a second species being resistant to gaseous sterilizing media, and the third species being resistant to radiation.

A preferred embodiment of a sterilization indicator of the present invention is illustrated in FIGS. 1 and 2. The device includes an outer container 40, having substantially gas non-absorptive and liquid impermeable walls 42 and an open end 44. Tube 40 contains a carrier 46, such as a strip of filter paper, bearing a predetermined amount of active enzyme and/or a predetermined number of viable microorganisms. Tube 40 also includes a normally sealed, pressure-openable inner container 48, such as a frangible glass ampoule, containing an aqueous nutrient growth medium and/or a suitable enzyme substrate dissolved or suspended in an aqueous buffered solution 50. The enzyme substrate is stable at temperatures between about 20° and 180° C. and is capable of reacting with active enzyme to yield a luminescent, fluorescent, colored or radioactive material. The aqueous nutrient medium is capable, with incubation, of promoting growth of viable microorganisms when contacted therewith. The carrier 46 is located at the bottom closed end of the outer container 40, and a barrier 47 is positioned like a plug between the carrier 46 and the pressure-openable inner container 48. The open end 44 of the outer container 40 is covered by a gas-transmissive, bacteria-impermeable closure member 52.

The outer container 40 has at least one opening therein to permit the sterilant (e.g., steam, ethylene oxide) to contact the source of active enzyme or microorganisms during sterilization. This opening is normally covered with a gas-transmissive, bacteria-impermeable means, such as a sheet. The sheet 52 may be sealed to the open end 44 of the outer container 40 by, e.g., heat or adhesive sealing, or by means of a closure device 56, such as a cap. During sterilization with a gaseous sterilization agent, the gaseous sterilant permeates the sheet 52 and passes through the interior of the outer container to contact the enzyme carrier 46.

Outer container 40 is made from material which will withstand the high temperatures encountered in steam sterilizers. Conventional steam sterilizers generally reach temperatures on the order of 121° C.-135° C. Additionally, the walls of container 40 must be substantially impermeable to gases and liquids. Outer container 40 which contains the carrier 46 coated with viable microorganisms and/or a source of active enzyme, and in which microorganism growth occurs or active enzyme reacts with the enzyme substrate during incubation, is preferably translucent (including "transparent") so that a change in luminescence or color may be visually observed without disassembling the indicator device. Preferably, also, the outer container 40 is sufficiently deformable so that the pressure-openable inner compartment 48 is ruptured when the outer compartment 40 is deformed, by using external pressure. Container 40 can be made by injection molding or extruding suitable materials, including polycarbonate, polypropylene, polyamides, polymethylpentenes and various polyesters. Polypropylene is the preferred material. These materials are sufficiently temperature resistant to withstand steam or dry heat sterilization cycles, non-absorbent of gaseous sterilizing media, liquid-impermeable, translucent or transparent and deformable.

The source of active enzymes and/or the microorganisms which are employed in the present invention normally are carried on a suitable carrier 46. It is contemplated, however, that the enzyme and/or microorganism may be carried by the inner walls of the outer container 40, or the outer walls of the inner container 48. Preferably, however, the enzyme source and/or microorganism are carried by the same or separate carriers. The carrier most preferably is water-absorbent, such as, filter paper, and should not inhibit microorganism growth or enzyme activity. However, other sheet-like materials such as cloth, nonwoven polypropylene, rayon or nylon, and microporous polymeric materials are also useful. However, metal foil substrates, for example, aluminum or stainless steel may be used, as well as substrates of glass (e.g., glass beads or glass fibers), porcelain, or plastic. Additionally, the carrier can be constructed of a combination of materials such as paper secured to a plastic or glass backing strip.

To assure reproducibility, it is desired that outer container 40 contain a predetermined amount of active enzyme and/or a predetermined number of viable microorganisms. This is readily accomplished with isolated enzyme by using general methods of protein purification, such as salt fractionation, chromatography and electrophoresis as described in Colowick, S., and Kaplan, N. O. (Eds), *Methods in Enzymology*, Academic Press, New York, Vols. I-VII, (1957-1964), incorporated herein by reference. Preferably the initial concentration of isolated enzyme is between about $1 \times 10^{-10}$ and $5 \times 10^{-2}$ units, more preferably between about $1 \times 10^{-8}$ and $5 \times 10^{-3}$ units of enzyme, and most preferably between about $1 \times 10^{-7}$ and $1 \times 10^{-3}$ units. Where a microorganism is utilized, an approximate number of bacterial or fungal spore is obtained by preparing a spore suspension having a known volumetric spore concentration, moistening the carrier 46 (e.g., filter paper) with a small, predetermined volume of the suspension, and drying the carrier. This method permits the approximate number of spores contained on the carrier to be easily calculated. Other methods, of course, may also be employed. Where the microorganism is *Bacillus stearothermophilus* or *Bacillus subtilis* the preferred number of microorganisms is about $1 \times 10^2$ to $1 \times 10^8$ microorganisms. Where the microorganism is *B. stearothermophilus*, about $1 \times 10^3$ to $1 \times 10^7$ microorganisms is preferred. Where the microorganism is *B. subtilis*, about $1 \times 10^6$ to $1 \times 10^8$ microorganisms is preferred. Where the microorganism is utilized as the source of the enzyme, the microorganism population which should be used will depend on the activity of the enzyme in that organism. The enzyme activity is dependent upon the culture conditions and strain selection of the microorganism, but can be regulated by adjusting the microorganism population.

Where an enzyme source of the type described hereinabove is used to monitor sterilization efficacy, an aqueous solution of an appropriate enzyme substrate system is normally included in pressure-openable, inner container 48. In the context of this application, an enzyme substrate system is by definition a substance or mixture of substances acted upon by an enzyme and converted into an enzyme-modified product. In general, the enzyme-modified product is a luminescent, fluorescent, colored or radioactive material. However, the enzyme substrate system can consist of a compound which when reacted with the enzyme, will yield a product which will react with an additional compound or composition to yield a luminescent, fluorescent, colored or radioactive material. Preferably, where the substrate system is to be included in the indicator device during sterilization, the substrate must not spontaneously break down or convert to a detectable product during sterilization or incubation. For example, in devices used to monitor steam and dry heat sterilization, the substrate must be stable at temperatures between about 20° and 180° C. The prior art includes a number of fluorogenic and chromogenic substrates for the detection of enzymes of diverse origin which are known, commercially available, and have been used in a variety of enzymatic procedures. (M. Roth, *Methods of Biochemical Analysis*, Vol. 17, D. Block, Ed., Interscience Publishers, New York, 1969, p. 189; S. Udenfriend, *Fluorescence Assay in Biology and Medicine*, Academic Press, New York, 1962, p. 312; and D. J. R. Lawrence, "Fluorescence Techniques for the Enzymologist", *Methods in Enzymology*, Vol 4, S. P. Colowick and N. O. Kaplan, Eds., Academic Press, New York, p. 174, incorporated herein by reference.) There are two basic types of enzyme substrate systems described for the detection of specific enzymes. The first type of substrate system can be either fluorogenic or chromogenic, and can be given a chemical formula such as, AB. When acted upon by the enzyme, AB, breaks down to A + B. B, for example, would be either fluorescent or colored. A specific example of a fluorogenic substrate of this type would be 4-methylumbelliferyl phosphate. In the presence of the enzyme phosphatase, the substrate will be broken down into 4-methylumbelliferone and phosphate. Other fluorogenic substrates of this type include the derivatives of 4-methylumbelliferyl, 7-amido-4-methylcoumarin, indoxyl and fluorescein, listed below. An example of a chromogenic substrate of this type is 5-bromo-4-chloro-3-indolyl phosphate. In the presence of phosphatase, the substrate will be broken down into indigo blue and phosphate. Other chromogenic substrates of this type include derivatives of 5-bromo-4-chloro-3-indolyl, nitrophenol and phenolphtalein, listed below.

The second type of substrate system commonly used for the detection of enzymes can be given the chemical formula CD, for example, which will be converted by a specific enzyme to C+D. However, neither C nor D will be fluorescent or colored, but D is capable of being further reacted with compound Z to give a fluorescent or colored compound, thus indicating enzyme activity. A specific fluorogenic example of this type is the amino acid lysine. In the presence of the enzyme lysine decarboxylase, lysine loses a molecule of $CO_2$. The remaining part of the lysine is then called cadaverine, which is strongly basic. A basic indicator such as 4-methylumbelliferone can be incorporated and will fluoresce in the presence of a strong base. A chromogenic substrate of this type would be 2-naphthyl phosphate. The enzyme phosphatase, reacts with the substrate to yield $\beta$-naphthol. The liberated $\beta$-naphthol reacts with a chromogenic reagent containing 1-diazo-4-benzoylamino-2,5-diethoxybenzene, commercially available as "Fast Blue BB Salt" from Sigma Chemical, to produce a violet color. Other examples of this type are listed under the naphthyl derivatives below.

Thus, from the foregoing one can readily appreciate that it is possible to determine the presence of specific enzymes in microorganisms through a variety of approaches.

A preferred enzyme substrate system is a fluorogenic one, defined herein as a compound capable of being enzymatically modified, e.g., by hydrolysis, to give a derivative fluorophor which has an appreciably modified or increased fluorescence.

It is understood that the fluorogenic compounds are in themselves either non-fluorescent or meta-fluorescent (i.e., fluorescent in a distinctly different way e.g., either by color or intensity, than the corresponding enzyme-modified products) and appropriate wavelengths of excitation and detection, in a manner well known to users of fluorometric instrumentation, are used to separate the fluorescence signal developed by the enzyme modification from any other fluorescence that may be present.

The prior art includes a number of fluorogenic substrates for enzymes of diverse origin which are known, commercially available, and have been used in enzymological procedures. Among these are a variety of fluorogenic 4-methylumbelliferyl derivatives (hydrolysable to 4-methylumbelliferone); derivatives of 7-amido-4-methyl-coumarin, e.g. GB Patent No. 1,547,747 and European Patent No. 0,000,063 (Ajinomoto), both patents incorporated herein by reference; diacetylfluorescein derivatives; and fluorescamine.

Useful 4-methylumbelliferyl derivatives include: 4-methylumbelliferyl-2-acetamido-4, 6-O-benzylidene-2-deoxy-$\beta$-D-glucopyranoside; 4-methylumbelliferyl acetate; 4-methylumbelliferyl-N-acetyl-$\beta$-D-galactosaminide; 4-methylumbelliferyl-N-acetyl-$\alpha$-D-glucosaminide; 4-methylumbelliferyl-N-acetyl-$\beta$-D-glucosaminide; 2'-(4-methylumbelliferyl)-$\alpha$-D-N-acetyl neuraminic acid; 4-methylumbelliferyl-$\alpha$-L-arabinofuranoside; 4-methylumbelliferyl-$\alpha$-L-arabinoside; 4-methylumbelliferyl butyrate; 4-methylumbelliferyl $\beta$-D-cellobioside; methylumbelliferyl-$\beta$-D,N,N'-diacetyl chitobioside; 4-methylumbelliferyl elaidate; 4-methylumbelliferyl-$\beta$-D-fucoside; 4-methylumbelliferyl $\alpha$-L-fucoside; 4-methylumbelliferyl-$\beta$-L-fucoside; 4-methylumbelliferyl-$\alpha$-D-galactoside; 4-methylumbelliferyl-$\beta$-D-galactoside; 4-methylumbelliferyl-$\alpha$-D-glucoside; 4-methylumbelliferyl-$\alpha$-D-glucoside; 4-methylumbelliferyl-$\beta$-D-glucuronide; 4-methylumbelliferyl-p-guanidinobenzoate; 4-methylumbelliferyl heptanoate; 4-methylumbelliferyl-$\alpha$-D-mannopyranoside; 4-methylumbelliferyl-$\beta$-D-mannopyranoside; 4-methylumbelliferyl oleate; 4-methylumbelliferyl palmitate; 4-methylumbelliferyl phosphate; 4-methylumbelliferyl propionate; 4-methylumbelliferyl stearate; 4-methylumbelliferyl sulfate; 4-methylumbelliferyl-$\beta$-D-N, N', N''-triacetylchitotriose; 4'-methylumbelliferyl-2,3,5-tri-o-benzoyl-$\alpha$-L-arabinofuranoside; 4-methylumbelliferyl-p-trimethylammonium cinnamate chloride; and 4-methylumbelliferyl-$\beta$-D-xyloside.

Useful 7-amido-4-methylcoumarin derivatives include: L-alanine-7-amido-4-methylcoumarin; L-proline-7-amido-4-methylcoumarin; L-tyrosine-7-amido-4-methylcoumarin; L-leucine-7-amido-4-methylcoumarin; L-phenylalanine-7-amido-4-methylcoumarin; and 7-glutarylphenylalanine-7-amido-4-methylcoumarin.

Useful peptide derivatives of 7-amido-4-methyl coumarin include: N-t-BOC-Ile-Glu-Gly-Arg 7-amido-4-methylcoumarin; N-t-BOC-Leu-Ser-Thr-Arg 7-amido-4-methylcoumarin; N-CBZ-Phe-Arg 7-amido-4-methylcoumarin; Pro-Phe-Arg 7-amido-4-methylcoumarin; N-t-BOC-Val-Pro-Arg 7-amido-4-methylcoumarin; and N-glutaryl-Gly-Arg 7-amido-4-methylcoumarin.

Useful diacetylfluorescein derivatives include fluorescein diacetate, fluorescein di-($\beta$-D-galactopyranoside), and fluorescein dilaurate.

Where the enzyme whose activity is to be detected is alpha-D-glucosidase, chymotrypsin, or fatty acid esterase, e.g., from *Bacillus stearothermophilus*, the fluorogenic enzyme substrate is most preferably 4-methylumbelliferyl-alpha-D-glucoside, 7-glutarylphenylalanine-7-amido-4-methyl coumarin, or 4-methylumbelliferyl heptanoate, respectively. Where the enzyme whose activity is to be detected is alpha-L-arabinofuranosidase, e.g., derived from *Bacillus subtilis*, a most preferred fluorogenic enzyme substrate is 4-methylumbelliferyl-alpha-L-arabinofuranoside. Where the enzyme whose activity is to be detected is beta-D-glucosidase, e.g., derived from *Bacillus subtilis*, a most preferred fluorogenic enzyme substrate is 4-methylumbelliferyl-beta-D-glucoside.

Another useful enzyme substrate system is a chromogenic compound capable of being enzymatically modified to give a derivative chromophor, or a product which reacts with another compound to give a derivative chromophor, which chromophor has a different or more intense color. It is understood that the chromogenic compounds are in themselves either non-colored or colored in a distinctly different way, e.g., either by color or intensity, than the corresponding enzyme-modified products. Appropriate wavelengths of excitation and detection, in manners well known to users of colorometric instrumentation are used to separate the colored signal developed by the enzyme modification from any other color that may be present.

A number of chromogenic substrates have been used in enzymological procedures. Among the useful chromogenic substrates are 5-bromo-4-chloro-3-indolyl derivatives; nitrophenyl derivatives; indoxyl derivatives; and phenolphtalein derivatives.

Useful 5-bromo-4-chloro-3-indolyl derivatives include 5-bromo-6-chloro-3-indolyl acetate, 5-bromo-4-chloro-3-indolyl acetate, 5-bromo-4-chloro-3-indoxyl-$\beta$-D-galactopyranoside, 5-bromo-4-chloro-3-indolyl-1,3-diacetate, 5-bromo-4-chloro-3-indolyl-$\beta$-D-fucopyranoside, 5-bromo-4-chloro-3-indolyl-$\beta$-D-glucopyranoside, 5-bromo-4-chloro-3-indolyl-$\beta$-D-glucuronic acid, 5-bromo-4-chloro-3-indolyl phosphate, and 5-bromo-4-chloro-3-indolyl sulfate.

Useful nitrophenyl derivatives include p-nitrophenol and o-nitrophenol derivatives. Particularly useful p-nitrophenols include diethyl-p-nitrophenyl phosphate; di-p-nitrophenyl phosphate; p-nitrophenyl-2-acetamido-2-deoxy-3-O-$\beta$-galactopyranosyl-$\beta$-glucopyranoside; p-nitrophenyl-2-acetamido-2-deoxy-$\beta$-glucopyranoside; p-nitrophenyl acetate; p-nitrophenyl-N-acetyl-$\beta$-D-glucosaminide; p-nitrophenyl-$\beta$-D-N,N'-diacetylchitobioside; p-nitrophenyl-$\alpha$-glucopyranoside; p-nitrophenyl-$\alpha$-maltoside; p-nitrophenyl-$\beta$-maltoside; p-nitrophenyl-$\alpha$-mannopyranoside; p-nitrophenyl-$\beta$-mannopyranoside; p-nitrophenyl myristate; p-nitrophenyl palmitate; p-nitrophenyl phosphate; tris(p-nitrophenyl)phosphate; p-nitrophenyl-$\beta$-glucopyranoside; p-nitrophenyl-$\beta$-glucuronide; $\alpha$-p-nitrophenylglycerine; p-nitrophenyl-$\alpha$-rhamnopyranoside; p-nitrophenyl stearate; p-nitrophenyl sulfate; p-nitrophenyl-2,3,4,6-tetra-O-acetyl-$\beta$-glucosaminide; p-nitrophenyl thymidine monophosphate; p-nitrophenyl-2,3,4-tri-O-acetyl-$\beta$-glucuronic acid methyl ester; and p-nitrophenyl valerate.

Particularly useful o-nitrophenols include o-nitrophenyl acetate, o-nitrophenyl-$\beta$-glucoside and o-nitrophenyl-$\beta$-D-glucopyranoside. Other particularly useful nitrophenyl derivatives include nitrophenyl-$\beta$-fucopyranoside; nitrophenyl-$\alpha$-galactopyranoside; nitrophenyl-$\beta$-galactopyranoside; nitrophenyl butyrate; nitrophenyl caprate; nitrophenyl caproate; nitrophenyl caprylate; nitrophenyl laurate; and nitrophenyl propionate.

Useful indoxyl derivatives include indoxyl-acetate; indoxyl $\beta$-D-glucoside; 3-indoxyl sulfate; 3-indoxyl phosphate.

Useful phenolphtalein derivatives include: phenolphthalein dibutyrate; phenolphthalein diphosphate; phenolphthalein disulfate; phenolphthalein glucuronic acid; phenolphthalein mono-$\beta$-glucosiduronic acid; phenolphthalein mono-$\beta$-glucuronic acid; and phenolphthalein mono-phosphate.

All of the above-described chromogenic substrates will react directly with an appropriate enzyme to produce a chromophor.

Additional enzyme substrates containing 1-naphthyl, 2-naphthyl and Napthyl-AS-BI derivatives are usefully employed if the derivative enzyme modified product is further reacted with a chromogenic reagent, such as diazotized dyes, e.g., 1-diazo-4-benzoylamino-2,5-diethoxybenzene, (commercially available as "Fast Blue BB Salt" from Sigma Chemical), 1-diazo-4-benzoylamino-2,5-diethoxybenzene, p-diazo-2,5-diethoxy-N-benzoylanaline, 4-chloro-2-methylbenzene diazonium chloride, and o-aminoazotoluene diazonium salt, to produce a chromophor.

Particularly useful 1-napthyl derivatives include 1-naphthyl-N-acetyl-$\beta$-D-glucosaminide.

Particularly useful 2-naphthyl derivatives include 2-naphthyl-phosphate; 2-naphthyl-butyrate; 2-naphthyl-caprylate; 2-naphthyl-myristate; L-leucyl-2-naphthylamide; L-valyl-2-naphthylamide; L-cystyl-2-naphthylamide; N-benzoyl-DL-arginine-2-naphthylamide; N-glutaryl-phenylalanine 2-naphthyl-amine; 2-naphthyl-phosphate; 6-Br-2-naphthyl-$\alpha$-D-galactopyranoside; 2-naphthyl-$\beta$-D-galacto-pyranoside; 2-naphthyl-2-D-glucopyranoside; 6-bromo-2-naphthol-$\beta$-D-glucopyranoside; 6-bromo-2-naphthyl-2-D-mannopyranoside; and 2-naphthyl-$\alpha$-L-fucopyranoside.

Particularly useful naphthyl-AS-BI derivatives include naphthyl-AS-BI-phosphate; and naphthyl-AS-BI-$\beta$-D-glucuronide.

Where the enzyme whose activity is to be detected is alpha-D-glucosidase, e.g., from *Bacillus stearothermophilus*, the chromogenic enzyme substrate is most preferably p-nitrophenyl-$\alpha$-glucopyranoside. Where the enzyme whose activity is to be detected is alpha-L-arabinofuranosidase, e.g., derived from *Bacillus subtilis*, a most preferred chromogenic enzyme substrate is p-nitrophenyl-alpha-L-arabinofuranoside. Where the enzyme whose activity is to be detected is beta-D-glucosidase, e.g., derived from *Bacillus subtilis*, a most preferred chromogenic enzyme substrate is p-nitrophenyl-$\beta$-D-glucopyranoside.

In order to carry out the method of the present invention, it is essential that the operator be knowledgable concerning the enzyme whose activity is to be detected, and the enzyme substrates which will react with the enzyme so as to produce a product which can be detected either by its fluorescence, color, etc. (See M. Roth, *Methods of Biochemical Analysis*, Vol. 7, D. Glock, Ed., Interscience Publishers, New York, N.Y., 1969, incorporated herein by reference.) The appropriate enzyme substrate to be utilized will depend upon the identity of the enzyme whose activity is under study.

The enzyme substrate system is preferably contained in inner container 48 in a buffered aqueous solution. The aqueous buffer acts as a reaction medium for the residual active enzyme and the enzyme substrate system after the inner container is ruptured. The ionic conditions of the buffered solution should be such that the enzyme and enzyme substrate are not effected. Preferably, an isotonic buffer, such as phosphate buffered saline solution, tris(hydroxymethyl) aminomethane-HCl solution, or acetate buffer is chosen. These preferred isotonic buffers are compatible with most fluorogenic and chromogenic enzyme substrates. Another consideration in choosing the buffers is its influence on the enzyme activity. For example, phosphate buffered saline contains a high concentration of inorganic phosphate which is a strong competitive inhibitor of alkaline phosphatase. For this enzyme, a Tris-HCl buffer is, therefore, advised.

The concentration of enzyme substrate present in the aqueous buffer is dependent upon the identity of the particular substrate and enzyme which is to be detected, the amount of enzyme-product that must be generated to be detectable, either visually or by instrument, and the amount of time that one is willing to wait in order to determine whether active enzyme is present in the reaction mixture. Preferably, the amount of enzyme substrate is sufficient to react with any residual active enzyme present, after the sterilization cycle, within about an eight hour period of time, such that at least $1 \times 10^{-8}$ molar enzyme-modified product is produced. Where the enzyme substrate is a 4-methylumbelliferyl derivative, it has been found that its concentration in the aqueous buffered solution is preferably between about $1 \times 10^{-5}$ and $1 \times 10^{-3}$ molar.

The aqueous solution containing the enzyme substrate preferably is adjusted to a pH of about 5.0 to 9.5, preferably about 7.5, in order to prevent autofluorescence of some basic fluorogenic substrates.

While the enzyme substrate system is normally included with the aqueous buffered reaction medium in inner container 48, it is contemplated that the enzyme substrate in dry form could be included in outer container 40 along with enzyme carrier 46. In fact, the active enzyme and its substrate could be present in dry form in the same carrier 46. In this construction, inner compartment 48 would preferably carry the aqueous reaction medium necessary for the active enzyme and its substrate to react.

Preferably, when a microorganism commonly used to monitor sterilization is included in the device (either as a source of active enzyme, or otherwise) and detection of microorganism survival by conventional methods is desired, inner container 48 contains an aqueous nutrient growth medium. Preferably, where the microorganism is a source of an enzyme useful to monitor sterilization or is included in addition to such an enzyme source, the nutrient growth media is compatible with most fluorogenic and chromogenic enzyme substrates and is not a competitive inhibitor for the enzyme. The types of nutrient media usefully employed in the present invention are widely known to the art. Examples of preferred nutrient media are aqueous solutions of soybean-casein digest broth, fluid thioglycollate and Dextrose Tryptone (Difco Laboratories, Inc.). A modified tryptic soy broth base, without glucose, is especially preferred. To avoid contamination, such aqueous nutrient media normally is sterilized after having been placed in the inner compartment. Commonly known microbial growth indicators, which change color in the presence of viable microorganisms, are preferably present in at least one of the containers. The growth indicator material preferably is soluble in, and imparts color (upon microorganism growth) to, the aqueous nutrient medium so that a change in color may be easily observed through the translucent walls of the outer container. In addition, the growth indicator material is preferably selected so that it will not interfere with the color or luminescence of the enzyme-modified product. Growth indicator materials which may be employed in the present invention are well known to the art and include pH-sensitive dye indicators (such as bromthymol blue, bromocresol purple, phenol red, etc.), oxidation-reduction dye indicators (such as methylene blue, etc.). Such materials commonly undergo changes in color in response to a phenomenon of microorganism growth, such as changes in pH, oxidation-reduction potentials, etc.

The inner container 48 which contains the aqueous solution of enzyme substrate and/or which contains the aqueous nutrient medium, is of material which is impermeable to gases and liquids and is capable of being opened upon the application of pressure thereto (i.e., "pressure openable") to permit the enzyme substrate and/or nutrient medium to enter the outer container. The inner container is preferably of frangible material, such as glass, and, is preferably snugly carried within the outer container in coacting relationship therewith to permit breakage or crushing of the inner container when the outer container is deformed. In another embodiment, the inner container may be sealed with a plug such that the plug is expelled to release the contents of the inner container upon application of pressure. In still another embodiment, the closure 56 may include an ampoule crushing device, as shown in U.S. Pat. No. 4,304,869, wherein the closure has tabs depending from the bottom of the closure device which upon depression of the closure device serve to crush the ampoule. Similarly, the device of the present invention may be used in a system having an ampoule crushing pin disposed in the bottom of the outer container 40.

Barrier 47 is positioned like a plug between the enzyme carrier 46 and the pressure-openable inner container 48. The barrier 47 is preferably made of materials which are non-fluorescent, for use with fluorogenic enzyme substrates, such as nonwoven webs made from fibers such as cotton, rayon, polypropylene, polypropylene/rayon blends, nylon or glass. Most preferably barrier 47 is constructed from a polypropylene nonwoven web, such as "Thinsulate ® 200-B brand Thermal Insulation", commercially available from 3M, St. Paul, Minn.

Barrier 47 serves to isolate the carrier 46 from the inner container 48. Barrier 47 is preferably made from a hydrophobic material so that enzyme-modified product and/or growing microorganisms concentrate around the carrier and do not diffuse rapidly into the area of the outer container which is on the other side of the barrier. Maintaining a higher concentration of growing microorganisms and/or enzyme-modified product in the lower portion of the indicator enables the growing microorganisms and/or enzyme-modified product, whether they be colored or luminescent to be detected after a shorter period of incubation than would be the case if the carrier 46 was reacted with the entire contents of inner container 48. In general, as illustrated in Example 1, preferred devices utilizing active enzyme detection methods and incorporating a barrier 47, provide reliable information on sterilization efficacy within about 10 minutes. Similar devices, not utilizing such a barrier, require about two hours to provide reliable sterilization efficacy information.

The outer container 40 has at least one opening therein to permit the sterilant (e.g., steam, ethylene oxide) to contact the microorganisms or source of active enzyme during sterilization. This opening is normally closed or plugged with a gas-transmissive, bacteria-impermeable closure means. Suitable means include closure member 52, made of fibrous materials such as cotton, glass wool, cloth, nonwoven webs made from polypropylene, rayon, polypropylene/rayon, nylon, glass or other fibers, filter papers, microporous hydrophobic and hydrophilic films, open celled polymeric foams, and semi-permeable plastic films such as those described in U.S. Pat. No. 3,346,464. Fibrous or cellular materials are preferred because of the ease with which such materials transmit sterilizing gases. Preferred closure member materials include hydrophobic materials such as nylon web, microporous hydrophobic film, or glass fiber nonwoven web. Especially preferred is a microporous hydrophobic film, commercially available from Celanese Separations Products, Charlotte, N.C., under the trade name "Celgard ® K-442 Microporous Film". In effect, the fibrous or cellular closure members serve as filters for bacteria and fungi and hence should have pore sizes no larger than about 0.5 microns (e.g., be capable of preventing the passage therethrough of particles having dimensions larger than about 0.5 microns). Alternatively, the closure means may be a tortuous pathway that is bacteria-impermeable, such as that described in U.S. Pat. No. 4,461,837, incorporated herein by reference, and in commonly assigned copending U.S. patent application (U.S. Ser. No. 249,982 filed Sep. 27, 1988).

The closure device 56 which holds the closure member 52 over the open end of outer container 42, is comprised of a top 57 and depending sidewalls 59. The closure has a hollow body open at the bottom, with the interior diameter of the closure being about equal to the exterior diameter of outer container 40, so that closure 56 may be frictionally engaged over the open end 44 of outer container 40. Cut within the sidewalls 59 are preferably a plurality of windows 58. When the indicator device is placed in a load to be sterilized, the closure 56 is placed over the opening in the outer container in such a manner that the exterior sidewalls 42 of the outer container do not block windows 58. In such a position, sterilant in the sterilizer may enter container 40 by flowing through windows 58. Upon completion of the sterilization cycle, the closure may be fully inserted by depressing it to force the sidewalls 42 of the outer container into engagement with the interior surface of top 57 thereby blocking windows 58. The interior of the container 40 is then sealed from the outside environment. The closure device 56 can be made from any material that will withstand the sterilization temperatures. As in the case of the container 40, suitable materials include polycarbonate, polypropylene, polyamides, polymethylpentenes and various polyesters, with polypropylene being preferred.

In use, the sterility indicator depicted in FIGS. 1 and 2 is placed in a sterilizer chamber together with a number of items to be sterilized by, for example, steam or ethylene oxide gas. When the indicator is in the sterilizer, the closure 56 is in the open position, such that windows 58 are open permitting entry of the sterilant. When the sterilizing agent is introduced into the chamber, the sterilant permeates through the closure member 52 and passes barrier 47 to inactivate the enzyme and/or kill the test microorganisms present on carrier 46. At the end of the sterilization cycle, the sterilant is replaced with filtered air. The sterility indicator is withdrawn from the sterilizer, the closure 56 is fully inserted to block windows 58, and glass ampoule 48 is broken by, for example, finger pressure, causing the aqueous solution of enzyme substrate and/or nutrient growth media to contact the carrier 46. The indicator is then placed in a suitable incubating environment (e.g. the indicator may be placed in warm water). The period of incubation will depend upon whether or not a source of enzyme useful to monitor sterilization efficacy and an enzyme substrate are included in the indicator. If they are included, incubation is continued for a period of time and under conditions sufficient to liberate a detectable amount of the enzyme-modified product, assuming that any of the enzyme remains active. In general, the amount of product which is detectable by known methods is at least $1 \times 10^{-8}$ molar. Preferably, the incubation conditions are sufficient to generate at least $1 \times 10^{-8}$ molar of enzyme-modified product, more preferably, about $1 \times 10^{-6}$ to $1 \times 10^{-5}$ molar of enzyme-modified product. The incubation time and temperature needed to produce a detectable amount of enzyme-modified product will depend upon the identity of the enzyme and the substrate, and the concentrations of each present in the reaction mixture. In general, the incubation time required is between about 1 minute and 12 hours, and the incubation temperature is between about 20° and 70° C. Preferably, where *Bacillus subtilis* or *Bacillus stearothermophilus* is the source of the enzyme, the incubation time required is between about 10 minutes and 3 hours, and the incubation temperature required is between about 30° and 40° C., and between about 52° and 65° C., respectively.

When a test microorganism is included in the indicator (either as the source of active enzyme, alone, or in addition to a source of active enzyme) the indicator also includes nutrient growth media and a growth indicator. The device is incubated preferably at about 56° C. for less than 24 hours, in preferred embodiments for about 8 hours. Any test microorganisms not killed during the sterilization cycle will begin to germinate and grow during incubation, causing the detector material contained in the indicator to change color.

After the appropriate incubation period, the occurrence of a change in color or luminescence is observed or measured spectrophotometrically through the translucent walls 42 of the outer container 40, and indicates that the sterilization cycle had not inactivated all the active enzyme or killed all the microorganisms present on the carrier 46 hence indicating that the sterilization cycle was perhaps insufficient to completely sterilize the items in the sterilizer. The absence of any change in color or luminescence indicates that the sterilization cycle had been sufficient to inactivate all of the enzyme or kill all of the test microorganisms on the carrier 46, and hence was sufficient to sterilize the items in the sterilizer.

A preferred method of monitoring the fluorescence of an indicator of this invention is a fluorimeter designed specifically for the devices described in this invention. A fluorimeter eliminates the subjective interpretation encountered when attempting to visually differentiate between low levels of fluorescent product and background or no fluorescence. A fluorimeter can be calibrated to detect a minimum amount of fluorescent product within a given incubation period.

A particularly preferred fluorimeter, designed for use with the devices of this invention, consists of a chamber designed to block ambient light while positioning the outer container of the indicator such that the enzyme carrier within can be illuminated with a 365 nm wavelength ultraviolet light, and a photodiode can detect any resultant fluorescence in the 460 nm wavelength region. The fluorimeter is calibrated to detect at least $1.0 \times 10^{-5}$M 4-methylumbelliferone.

Several methods can be used to differentiate the fluorescent positive devices from the non-fluorescent or negative devices. In the first approach, a fluorescent threshold limit equivalent to the fluorescence produced by $1 \times 10^{-5}$M 4-methylumbelliferone is established in the fluorimeter. When a test sample with sufficient active enzyme converts enough substrate to exceed the threshold limit, after the enzyme carrier is allowed to react with the substrate at, e.g., 56° C. for 15 minutes, the fluorimeter indicates a positive sample by illuminating, for example, a red light. If the fluorescent product produced by reaction of the enzyme and its substrate does not exceed the threshold limit, after the 15 minute incubation, for example, the fluorimeter will indicate a negative or non-fluorescent sample, with, for example, a green light.

In the second approach, the fluorimeter measures the initial fluorescence, at the beginning of the incubation period. The fluorimeter chamber is heated to the optimum temperature for the specific enzyme being tested in the device. In the case of the enzyme alpha-D-glucosidase derived from *Bacillus stearothermophilus*, the temperature is 56° C. During the incubation period, the fluorimeter continues to monitor the fluorescence and will indicate a positive fluorescent sample when at least a 5% increase in intensity above the initial fluorescence is detected by, for example, a red light. If less than a 5% increase occurs within the established incubation time, the fluorimeter will indicate a negative or non-fluorescent sample by, for example, activating a green light.

FIGS. 3 and 4 illustrate an alternative preferred embodiment of the sterilization indicator of the present invention. The device includes, as does the device of FIGS. 1 and 2, an outer container 70, with gas non-absorptive and liquid impermeable walls 72 and an open end 74; a pressure-openable inner container 78 within outer container 70, containing an aqueous solution 80 of nutrient growth medium and/or enzyme substrate; and a gas-transmissive, bacteria-impermeable closure member 82, which is held over the open end 74 of the outer container by cap 86. The carrier 77 which carries viable microorganism or another source of active enzyme is attached to a wick strip 76 by, for example, adhesive or heat sealing. The wick strip can be made from any water-absorbent material, such as filter paper, cloth, or rayon. Additionally, the wick strip can be constructed of a combination of materials such as paper secured to a plastic or glass backing strip. Preferably wick strip 76 is prepared from polyethylene coated paper. Preferably, the dimensions of the wick strip and the placement of the enzyme carrier on the wick strip are such that when the inner-container is ruptured the liquid therein is contained within the lower portion of the outer container 40 and below the carrier 77. The aqueous solution 80 travels up the wick strip 76 to carrier 77. The growing microorganisms and/or enzyme-modified product concentrates on the carrier 77 and its presence is detected in a shorter period of time than would be the case if the carrier was exposed to the entire solution present in the inner container 78.

The sterility indicator of the present invention has been described primarily with reference to sterilizing media such as ethylene oxide, steam and the like. The indicator is not, however, limited to these uses, and may as well be used to indicate the efficacy of other sterilizing media, such as dry heat, radiation, propylene oxide, methyl bromide, ozone, chlorine dioxide, formaldehyde, and other gaseous and liquid agents.

The invention will be illustrated by the following non-limiting examples, in which all percentages are percent by weight, unless otherwise indicated.

EXAMPLE 1

This example illustrates the correlation between the fluorescent results of the enzymatic detection method described in this application, and the results of conventional spore survival methods of detection. This example also illustrates the shorter read-out times which can be achieved with the device illustrated in FIGS. 1 and 2, which utilizes a barrier 47 between the ampoule 48 and the enzyme carrier 46.

*Bacillus stearothermophilus* commercially available as "ATCC 7953" from American Type Culture Collection, Rockville, Md., was grown overnight (16 hours) at 58° C. in tryptic soy broth. This culture was used to inoculate the surface of agar plates consisting of 8 g/l nutrient broth, 4 g/l yeast extract, 0.1 g/l manganese chloride and 20 g/l agar at pH 7.2. Plates were incubated at 58° C. for 72 hours. Spores were scraped from the plates and suspended in sterile distilled water. The spores were separated from the vegetative debris by centrifuging the suspension at 7000 rpm and 4° C. for 20 minutes. The supernatant was poured off and the spores were resuspended in sterile distilled water. This cleaning procedure was repeated several times. The *Bacillus stearothermophilus* spores were coated on 6.35 mm (¼ inch) in diameter filter paper discs, commercially available as "S&S · #903 Grade Filter Paper" from Schleicher & Schuell, Inc., Keene, N.H., at a population of $1.6 \times 10^6$ spores per disc. This was accomplished by preparing a suspension of the *B. stearothermophilus* spores in water at a concentration of $1 \times 10^8$ spore/ml, pipetting 10 μl of this suspension on each filter paper disc and allowing the discs to dry.

Two types of devices were constructed as follows. The first device was constructed as illustrated in FIGS. 1 and 2, with the spore coated strip 46 on the bottom of the outer container 40 and a barrier 47 between the ampoule 48 and the spore strip. A 1.75 mm (11/16 inch) diameter disc of polypropylene blown microfiber material, with a weight of 200 g/m², commercially available as "Thinsulate ® 200-B brand Thermal Insulation" from 3M, St. Paul, Minn., was used as the barrier 47. The ampoule 48 contained 0.67 ml nutrient medium, consisting of 17 g of a bacteriological peptone and 0.17 g of L-alanine, as well as 0.1 g 4-methylumbelliferyl-alpha-D-glucoside, commercially available from Sigma Chemical Company, St. Louis, Mo., dissolved in 200 μl of N, N-dimethylformamide, and 0.03 g bromocresol purple pH indicator dye, per liter of water. The pH of the enzyme substrate and nutrient medium solution was adjusted to 7.6 with 0.1N sodium hydroxide.

The outer container 40 and the cap 56 are both made from polypropylene. The outer container was 5.08 cm (2.0 inches) long, with an outer diameter of 85.1 mm (0.335 inches) and an internal diameter of 77.0 mm (0.303 inches). The cap was 1.275 cm (0.510 inch) long with an internal diameter of 83.3 mm (0.328 inch). The inner ampoule 48 was made of glass and was 3.96 cm (1.56 inches) long, with an outer diameter of 65.5 mm (0.258 inches), and a wall thickness of 2.5 mm (0.010 inches). The closure member 52 was a 1.27 mm (½ inch) in diameter piece of polypropylene, commercially available as "Celgard ® K-442 Microporous Film", from Celanese Separations Products, Charlotte, N.C.

The second device was identical to the first device, except that the barrier 47 was omitted.

Five unit batches of both types of devices were placed in metal instrument trays and exposed at 132° C. in a gravity displacement steam sterilizer, commercially available as an "Amsco Eagle ™ Model 2013 Sterilizer", from American Sterilizer Company, Erie, Pa., for 0.5, 1.0, 1.5, 2.0, 2.5 and 3.0 minutes. After exposure the inner ampoules containing the enzyme substrate and nutrient medium were crushed and the units were incubated at 56° C. An ultraviolet light ($\lambda=366$ nm) was used to illuminate the vials for visually read fluorescence after 10 min., 20 min., 30 min., 60 min., 120 min., 180 min., and 240 minutes of incubation. Additionally, spore growth, as indicated by a color change from purple to yellow, was determined visually after 24 hours of incubation at 56° C.

The results are reported in Table I.

yellow, was determined visually after 24 hours of incubation.

The results are reported in Table II.

TABLE I

| Device | Exposure Time (minutes) | FLUORESCENCE Incubation Time (Minutes) at 56° C. Number Positive/5 Tested | | | | | | | Spore Growth at 24 hr. |
|---|---|---|---|---|---|---|---|---|---|
| | | 10 | 20 | 30 | 60 | 120 | 180 | 240 | |
| 1 | 0.5 | 5 | 5 | 5 | 5 | 5 | 5 | 5 | 5 |
| (Spore Strip on Bottom | 1.0 | 5 | 5 | 5 | 5 | 5 | 5 | 5 | 5 |
| with Barrier Material) | 1.5 | 5 | 5 | 5 | 5 | 5 | 5 | 5 | 5 |
| | 2.0 | 3 | 3 | 3 | 3 | 3 | 3 | 3 | 3 |
| | 2.5 | 0 | 0 | 0 | 0 | 2* | 2* | 3* | 0 |
| | 3.0 | 0 | 0 | 0 | 0 | 0 | 0 | 0 | 0 |
| 2 | 0.5 | 0 | 0 | 0 | 5 | 5 | 5 | 5 | 5 |
| (Spore Strip on Bottom | 1.0 | 0 | 0 | 0 | 5 | 5 | 5 | 5 | 5 |
| Without Barrier | 1.5 | 0 | 0 | 0 | 5 | 5 | 5 | 5 | 5 |
| Material) | 2.0 | 0 | 0 | 0 | 5 | 5 | 5 | 5 | 5 |
| | 2.5 | 0 | 0 | 0 | 0 | 3* | 3* | 3* | 1 |
| | 3.0 | 0 | 0 | 0 | 0 | 0 | 0 | 0 | 0 |

*Indicates on or more false positive reactions which appear to be the result of residual enzyme activity following spore inactivation in marginal sterilization cycles The data in Table I illustrates that the presence of active alpha-D-glucosidase can be detected by the methods described in this application much more quickly than can the detection of viable spores. The data illustrates that the detection of active enzyme in a device can be used to predict eventual spore growth in the device.

The data in Table I illustrates that using device 1 (with a barrier between the ampoule and the spore strip) enzyme activity can be detected after 10 minutes for all units which show spore growth after 24 hours of incubation. Using device 2 (without barrier material), 2 hours of incubation is required in order to detect enzyme activity in all units which show spore growth after 24 hours of incubation.

EXAMPLE 2

Devices were constructed as illustrated in FIGS. 3 and 4, with the enzyme carrier 77 on a wick 76. One spore strip, prepared in accordance with Example 1, was heat sealed to one end of a 0.10 mm thick polyethylene coated paper, 6.35 mm × 28.58 mm. The ampoule 78 contained 5 ml/l of a nonionic surfactant, commercially available as "Tween TM 80 Polyoxyethylene Sorbitan Monooleate", from ICI Americas, Inc., Wilmington, Del., to aid in the wetting of the spore carrier, as well as the enzyme substrate, nutrients and indicators present in the solution of Example 1. The outer vial, cap and inner ampoule were identical to those used in the devices of Example 1. The gas-permeable, bacteria-impermeable member was a sterilization grade filter paper.

Five unit batches of devices were placed in metal instrument trays and exposed at 132° C. in a gravity displacement steam sterilizer, commercially available as an "Amsco Eagle TM Model 2013 Sterilizer", from American Sterilizer Company, Erie, Pa., for 0.5, 1.0, 1.5, 2.0, 2.5 and 3.0 minutes. After exposure the inner ampoules were crushed and the devices were incubated at 56° C. An ultraviolet light ($\lambda = 366$ nm) was used to illuminate the vials for visually read fluorescence after 10 min., 20 min., 30 min., 60 min., 120 min., 180 min., and 240 minutes of incubation. Additionally, spore growth, as indicated by a color change from purple to yellow, was determined visually after 24 hours of incubation.

The results are reported in Table II.

TABLE II

| Exposure Time (minutes) | FLUORESCENCE Incubation Time (Minutes) at 56° C. Number Positive/5 Tested | | | | | | | 24 hr. Growth |
|---|---|---|---|---|---|---|---|---|
| | 10 | 20 | 30 | 60 | 120 | 180 | 240 | |
| 0.5 | 5 | 5 | 5 | 5 | 5 | 5 | 5 | 5 |
| 1.0 | 5 | 5 | 5 | 5 | 5 | 5 | 5 | 5 |
| 1.5 | 5 | 5 | 5 | 5 | 5 | 5 | 5 | 5 |
| 2.0 | 0 | 0 | 0 | 0 | 4* | 5* | 5* | 0 |
| 2.5 | 0 | 0 | 0 | 0 | 0 | 0 | 0 | 0 |
| 3.0 | 0 | 0 | 0 | 0 | 0 | 0 | 0 | 0 |

*Indicates one or more false positive reactions which appear to be the result of residual enzyme activity following spore inactivation in marginal sterilization cycles The data in Table II illustrates that much quicker detection of spore survival can be achieved using the devices and enzyme detection methods of the present invention in contrast to standard 24 hour spore growth.

EXAMPLE 3

Bacillus stearothermophilus spores, prepared in accordance with Example 1, were coated and dried on 6.35×28.58 mm (¼×⅛ inch) carriers made of a filter paper, commercially available as "S&S #591A Grade Filter Paper" from Schleicher and Schuell, Inc. of Keene, N.H. at concentrations of $1.0 \times 10^7$, $7.5 \times 10^5$, $1.0 \times 10^5$, $1.7 \times 10^4$, $2.8 \times 10^3$ spores per carrier. Devices were assembled using these spore strips, as shown in FIGS. 1 and 2 and described as Device 1 in Example 1.

Three unit batches of devices were placed in metal instrument trays and exposed at 132° C. in a gravity displacement steam sterilizer, commercially available as an "Amsco Eagle TM Model 2013 Steam Sterilizer", from American Sterilizer Company, Erie, Pa., for 1.0, 1.5, 2.0, 2.5 and 3.0 minutes. After exposure the inner ampoules were crushed and the devices were incubated at 56° C. An ultraviolet light ($\lambda = 366$ nm) was used to illuminate the vials to visually detect fluorescence after 10 min., 20 min., 30 min., 60 min., 120 min., 180 min., 240 min., 300 min., and 360 minutes of incubation. Additionally, spore growth, as indicated by a color change from purple to yellow, was determined visually after 24 hours of incubation.

The results are reported in Table III.

TABLE III

| Spore Population | Exposure Time (minutes) | FLUORESCENCE Incubation Time (Minutes) at 56° C. Number Positive/3 Tested | | | | | | | | | Spore Growth at 24 hr. |
|---|---|---|---|---|---|---|---|---|---|---|---|
| | | 15 | 30 | 45 | 60 | 120 | 180 | 240 | 300 | 360 | |
| $1.0 \times 10^7$ | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 0 | 1* | 1* | 1* | 2* | 2* | 2* | 2* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| $7.5 \times 10^5$ | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 2* | 2* | 2* | 2* | 2* | 2* | 2* | 2* | 2* | 1 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| $1.0 \times 10^5$ | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 1* | 1* | 1* | 1* | 1* | 1* | 1* | 2* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| $1.7 \times 10^4$ | 1.0 | 0 | 0 | 2 | 2 | 3 | 3 | 3 | 3 | 3 | 3 |
| | 1.5 | 0 | 0 | 3* | 3* | 3* | 3* | 3* | 3* | 3* | 2 |
| | 2.0 | 0 | 0 | 0 | 0 | 0 | 0 | 0 | 0 | 0 | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| $2.8 \times 10^3$ | 1.0 | 0 | 0 | 0 | 0 | 0 | 3 | 3 | 3 | 3 | 3 |
| | 1.5 | 0 | 0 | 0 | 0 | 0 | 0 | 0 | 0 | 0 | 0 |
| | 2.0 | 0 | 0 | 0 | 0 | 0 | 0 | 0 | 0 | 0 | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |

*Indicates on or more false positives which appears to be the result of residual enzyme activity following spore inactivation in marginal sterilization cycles Table III illustrates that even with a low spore population, the spore survivors were predicted by enzyme activity (i.e., fluorescence) well before any growth of the organism was detected.

EXAMPLE 4

This example compares read-out times for devices employing different strains of *Bacillus stearothermophilus* spores. The following strains were tested: "ATCC 8005", commercially available from American Type Culture Collection, Rockville, Md.; spores obtained from growing the microorganism contained in three different commercially available biological indicators, "ATTEST TM Biological Indicator", 3M, St. Paul, Minn., "Proof PLUS TM Biological/Chemical Indicator", American Sterilizer Co., Erie, Pa., and "Assert TM Biological/Chemical Indicator", Surgicot, Smithtown, N.Y.; "NCTC 10003" commercially available from Nation Collection of Type Cultures, Colindale, London, England; "German Earthspore" obtained by culturing earth strips supplied by the Hygiene Institute of Hamburg, Hamburg, Germany, in tryptic soy broth after exposure at 121° C. for 5 minutes (the 5 min. exposure was used to kill all the vegetative organisms present in the earth so only *B. stearothermophilus* remains; and Scandinavian strain isolated from spore strips produced by Statens Institute for Falkehelse, Oslo, Norway.

All spores were grown on a nutrient agar medium as described in Example 1. The spores were centrifuged at 11,000 rpm for 5 hours at 4° C. in density gradient commercially available as Percoll ® from Pharmacia Fine-Chemicals AB, Uppsala, Sweden. After centrifuging the spores were resuspended in sterile distilled water. With the German Earthspore, two distinct layers of cells were isolated in the density gradient during centrifugation. Using phase contact microscopy, the bottom layer was found to be predominantly spores and the top layer was predominantly vegetative cells and vegetative debris with a small number of spores. Both layers were tested separately.

The spores were coated and dried on 6.35×28.58 mm (¼×1⅛ inch) strips of filter paper ("S&S 591A Grade Filter Paper") at a population of at least $1 \times 10^6$ per carrier. Devices were assembled as in Device 1, Example 1, except that in one batch of devices using the "ATCC 8005" spores, the enzyme substrate used was 4-methylumbelliferyl-beta-D-galactoside, commercially available from Sigma, 0.1 g/l dissolved in 200 μl N, N-dimethylformamide, instead of 4-methylumbelliferyl-alpha-D-glucoside, in order to detect the enzyme activity of beta-D-galactosidase on the "ATCC 8005" spores. Three unit batches were exposed at 132° C. for 1.0, 1.5, 2.0, 2.5 and 3.0 minutes in an "Amsco Eagle TM Model 2013 Steam Sterilizer". After exposure the inner ampoules were crushed and the units were incubated at 56° C. An ultraviolet light (λ=366 nm) was used to illuminate the vials for visually read fluorescence after 10 min., 20 min., 30 min., 60 min., 120 min., 180 min., and 240 minutes of incubation. Additionally, spore growth, as indicated by a color change from purple to yellow, was determined visually after 24 hours of incubation.

The results are reported in Table IV.

TABLE IV

| Strain | Exposure Time (minutes) | FLUORESCENCE Incubation Time (Minutes) at 56° C. Number Positive/3 Tested | | | | | | | | | Spore Growth at 24 hr. |
|---|---|---|---|---|---|---|---|---|---|---|---|
| | | 10 | 20 | 30 | 40 | 50 | 60 | 120 | 180 | 240 | |
| "ATCC 8005" | 1.0 | 3 | 3 | 3 | 3 | 3 | 3 | 3 | 3 | 3 | 3 |
| (enzyme substrate- | 1.5 | 0 | 1 | 1 | 1 | 1 | 1 | 2 | 2 | 2 | 3 |

TABLE IV-continued

| Strain | Exposure Time (minutes) | FLUORESCENCE Incubation Time (Minutes) at 56° C. Number Positive/3 Tested | | | | | | | | | Spore Growth at 24 hr. |
|---|---|---|---|---|---|---|---|---|---|---|---|
| | | 10 | 20 | 30 | 40 | 50 | 60 | 120 | 180 | 240 | |
| 4-methylumbelliferyl-α-D-glucoside) | 2.0 | 0 | 0 | 0 | 0 | 0 | 0 | 0 | 0 | 0 | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| "ATCC 8005" (enzyme substrate-4-methylumbelliferyl-β-D-galactoside) | 1.0 | 3 | 3 | 3 | 3 | 3 | 3 | 3 | 3 | 3 | 3 |
| | 1.5 | 0 | 2 | 3 | 3 | 3 | 3 | 3 | 3 | 3 | 3 |
| | 2.0 | 0 | 0 | 0 | 0 | 0 | 0 | 0 | 0 | 0 | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| "PROOF PLUS ™ Biological/Chemical Indicator" | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 1 | 3 | 3 | 3 | 3 | 3 | 3 | 3 | 3 | 3 |
| | 2.5 | 0 | 0 | 0 | 2 | 3 | 3 | 3 | 3 | 3 | 3 |
| | 3.0 | 0 | 0 | 0 | 0 | 0 | 0 | 0 | 0 | 0 | 0 |
| "ATTEST ™ Biological Indicator" | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 3 | 3 | 3 | 3 | 3 | 3 | 3 | 3 | 3 | 3 |
| | 2.5 | 0 | 0 | 0 | 0 | 3 | 3 | 3 | 3 | 3 | 3 |
| | 3.0 | 0 | 0 | 0 | 0 | 0 | 0 | 0 | 0 | 0 | 0 |
| "ASSERT ™ Biological/Chemical Indicator" | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 3 | 3 | 3 | 3 | 3 | 3 | 3 | 3 | 3 |
| | 2.5 | 0 | 0 | 0 | 0 | 1 | 1 | 3 | 3 | 3 | 3 |
| | 3.0 | 0 | 0 | 0 | 0 | 0 | 0 | 0 | 0 | 0 | 0 |
| "NCTC 10003" | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 3 | 3 | 3 | 3 | 3 | 3 | 3 | 3 | 3 | 3 |
| | 2.5 | 0 | 0 | 2 | 3 | 3 | 3 | 3 | 3 | 3 | 3 |
| | 3.0 | 0 | 0 | 0 | 0 | 0 | 0 | 0 | 0 | 0 | 0 |
| "German Earthspore" | 1.0 | 2 | 3 | 3 | 3 | 3 | 3 | 3 | 3 | 3 | 3 |
| | 1.5 | 0 | 2 | 3 | 3 | 3 | 3 | 3 | 3 | 3 | 3 |
| | 2.0 | 0 | 0 | 0 | 0 | 0 | 0 | 0 | 0 | 0 | 1 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| "German Earthspore" Vegatative + Spores | 1.0 | 0 | 3 | 3 | 3 | 3 | 3 | 3 | 3 | 3 | 3 |
| | 1.5 | 0 | 0 | 0 | 1 | 3 | 3 | 3 | 3 | 3 | 2 |
| | 2.0 | 0 | 0 | 0 | 0 | 0 | 0 | 0 | 0 | 1 | 2 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Scandinavian strain | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 0 | 0 | 0 | 0 | 1* | 2* | 2* | 2* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |

*Indicates one or more false positive reactions which appear to be the result of residual enzyme activity following spore inactivation in marginal sterilization cycles Table IV illustrates that all strains of *B. stearothermophilus* tested had enzyme activity (either alpha D-glucosidase or beta-D-galactosidase) that correlated with spore survival. In most units where spores survived, fluorescence was detected within 2 hours of incubation and in many units fluorescence was detected after 10 minutes of incubation. The layer of cells consisting mostly of vegetative cells from the German Earthspore also had enzyme survival following the sublethal exposures. This indicates that the alpha-D-glucosidase associated with vegetative cells could be used in this invention. Several units with the Scandinavian strain had enzyme survival and no growth of the organism with further incubation. This has been observed previously and occurs in marginal cycles. The enzyme remains active slightly longer than the spore, and this provides an additional safety margin by monitoring more of the cycles insuring sterility of the items in the sterilizer.

EXAMPLE 5

*Bacillus stearothermophilus* spores were coated on a variety of materials to compare the fluorescent readout time. The *B. stearothermophilus* spores were obtained, as described in Example 1, and were suspended in ethanol and deposited at approximately $1 \times 10^6$ spores per 6.35×28.58 mm (¼×1⅛ inch) strip of the following materials: polypropylene/rayon nonwoven web, commercially available as "Novonette ® Nonwoven Fabric #149-190" from Kendall Fiber Products Division; nylon nonwoven web, commercially available as "Novonette ® Nonwoven Fabric #149-000" from Kendall Fiber Products Division, Boston, Mass.; microporous hydrophobic film, commercially available as "Celgard ® Microporous Hydrophilic Film 2500" from Celanese Separations Products, Charlotte, N.C.; microporous hydrophilic film, commercially available as "Celgard ® Microporous Hydrophilic Film 3401" from Celanese Separations Products; aluminum foil commercially available from Reynolds, Metals Company, Richmond, Va.; filter paper, commercially available as "S&S 591A Grade Filter Paper" from Schleicher & Schuell; filter paper, commercially available as "S&S 903 Grade Filter Paper" from Schleicher & Schuell; and glass fiber nonwoven web, commercially available as "Manniglas #1267 Nonwoven Glass Fiber Paper" from Manning Paper Company, Division of Hammermill Paper Co., Troy, N.Y. Ten microliters of the suspended spores, i.e., $1 \times 10^6$ spores, were also deposited in polypropylene vials of the same dimensions as those described in Example 1.

Devices utilizing the spore strips were assembled in accordance with Example 1, Device 1, and as illustrated in FIGS. 1 and 2, except that a 1.75 mm (11/16 inch) in diameter piece of polypropylene nonwoven scrim, commercially available as "0.5 oz Celestra ™ Nonwoven Polypropylene" from Crown Zellerback Corp., Camas, Wash. was sandwiched between the spore strip 46 and the bottom of the outer vial. This sandwich insured wetting of the spore strips with nutrient media when ampoule 48 is broken, since the scrim acts as a wick to draw nutrient media past the hydrophobic nylon web, microporous hydrophobic film, aluminum foil, or glass fiber nonwoven web. Devices utilizing the spore coated vials were assembled in accordance with Example 1, Device 1, except that the device contained no spore strip or barrier. Three unit batches of the indicators were exposed in the "Amsco Eagle ™ Model 2013 Steam Sterilizer" at 132° C. for 1.0, 1.5, 2.0, 2.5 and 3.0 minutes. After exposure the ampoules containing the enzyme substrate solution and nutrient medium were crushed and the devices were incubated at 56° C. and checked for fluorescence using a longwave U.V. light ($\lambda = 366$) commercially available as a "Blak-Ray ® Lamp", Model UV L-21, from Ultraviolet Products, Inc., San Gabriel, Calif., every 15 minutes for 1 hour, and then hourly for up to 6 hours. Incubation was continued for 24 hours, and the devices were read for growth (yellow) or no growth (purple).

The results are reported in Table V.

TABLE V

| Carrier Material | Exposure Time (Minutes) | FLUORESCENCE Incubation Time (minutes) at 56° C. Number Positive/3 Tested | | | | | | | | | Spore Growth at 24 hr. |
|---|---|---|---|---|---|---|---|---|---|---|---|
| | | 15 | 30 | 45 | 60 | 120 | 180 | 240 | 300 | 360 | |
| Polypropylene/ rayon web ("Novonette ® Nonwoven Fabric") | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 3* | 3* | 3* | 3* | 3* | 3* | 3* | 3* | 3* | 1 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Microporous hydrophobic film ("Celgard ® Microporous Hydrophobic Film 2500") | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 0 | 0 | 0 | 2 | 2 | 3* | 3* | 3* | 2 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Aluminum foil | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 0 | 0 | 0 | 1* | 1* | 2* | 3* | 3* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Microporous hydrophilic film (Celgard ® Microporous Hydrophobic Film 3401") | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 0 | 0 | 1* | 3* | 3* | 3* | 3* | 3* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Nylon nonwoven web ("Novonette ™ Nonwoven fabric" #149-000) | 1.0 | 3 | 3 | 3 | 3 | 3 | 3 | 3 | 3 | 3 | 3 |
| | 1.5 | 2 | 2 | 2 | 2 | 3 | 3 | 3 | 3 | 3 | 2 |
| | 2.0 | 3 | 3 | 3 | 3 | 3 | 3 | 3 | 3 | 3 | 3 |
| | 2.5 | 0 | 0 | 0 | 0 | 0 | 2* | 2* | 2* | 2* | 0 |
| | 3.0 | 0 | 0 | 0 | 0 | 0 | 0 | 0 | 0 | 0 | 0 |
| Filter paper ("S&S 903 Grade Filter Paper") | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 3* | 3* | 3* | 3* | 3* | 3* | 3* | 3* | 3* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Filter paper ("S&S 591A Grade Filter Paper") | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 0 | 1* | 1* | 2* | 2* | 2* | 2* | 2* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Glass fiber web ("Manniglas #1267 Nonwoven Glass Fiber Paper") | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 1 | 1 | 2* | 3* | 3* | 3* | 3* | 3* | 3* | 1 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Polypropylene vials | 1.0 | 2 | 3 | 3 | 3 | 3 | 3 | 3 | 3 | 3 | 3 |
| | 1.5 | 2 | 2 | 3 | 3 | 3 | 3 | 3 | 3 | 3 | 3 |
| | 2.0 | 0 | 0 | 0 | 0 | 2 | 2 | 2 | 2 | 2 | 2 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |

*Indicates one or more false positive reactions which appear to be the result of residual enzyme activity following spore inactivation in marginal sterilization cycles In all the indicators with spores coated on carriers that survived the steam exposure, spore survival (by enzyme activity was) detected within 15 minutes. The indicators where the spores were coated directly on the vials required up to two hours to detect all instances where there was active alpha-D-glucosidase, and therefore spore survival. This increased time until reliable readout is a result of the fact that in the spore-coated vial indicators, the entire volume of medium must be monitored for fluorescence. In contrast, with the devices which use spore strips and a barrier between the ampoule and the spore strip, only the spore strip is viewed for fluorescence. The barrier acts as a semi-permeable membrane to allow a small volume of media and enzyme substrate to contact the spore carrier. Reaction of the enzyme on any portion of the carrier with the enzyme substrate can be seen in a much shorter time, than can reaction of enzyme with the entire contents of the ampoule.

EXAMPLE 6

"ATCC 9372" *Bacillus subtilis* was grown overnight (16 hours) at 37° C. in tryptic soy broth. This culture was used to inoculate the surface of agar plates consisting of 8 g/l nutrient broth, 0.011 g/l manganese sulfate and 20 g/l agar at pH 7.2. The plates were incubated at 37° C. for 6 days and the spores were scraped from the plates and suspended in sterile distilled water. The spores were separated from the vegetative debris by centrifuging the suspension at 7000 rpm and 4° C. for 20 minutes. The supernatant was poured off and the spores were resuspended in sterile distilled water. This cleaning procedure was repeated several times.

The *Bacillus subtilis* spores were coated at a population of $1.0 \times 10^8$ on $6.35 \times 28.58$ mm "S&S 591A Grade Filter Paper" strips. Devices were assembled using these spore strips, as shown in FIGS. 1 and 2, and as described in Example 1, Device 1. Three unit batches of these devices were preconditioned at 54° C. and 50% relative humidity for 30 minutes. The devices were then exposed for 15, 30, 60 and 120 minutes, at 54° C. and 50% relative humidity, to 600 mg/l of ethylene oxide in a Steri-Vac TM 400B Gas Sterilizer", commercially available from 3M Co., St. Paul, Minn., which had been modified in accordance with the "Association for the Advancement of Medical Instrumentation, Standard for BIER/EO Gas Vessels", AAMI BEOU-3/82. After exposure, the inner ampoules were removed from the devices and 0.67 ml of a solution which was identical to that contained in the inner ampoule, except that it contained 0.03 g/l of 2,3,5-triphenyl tetrazolium chloride (commercially available from ICN Pharmaceuticals Inc., Cleveland Ohio), instead of bromocresol purple pH indicator dye, and 0.1 g/l 4-methylumbelliferyl-beta-D-glucoside (commercially available from Sigma), in place of the 4-methylumbelliferyl-alpha-D-glucoside, was pipetted into the outer vial. The devices were incubated at 37° C. An ultraviolet light ($\lambda = 366$ nm) was used to illuminate the devices to visually detect fluorescence after 30 min., 60 min., 90 min., 120 min., 180 min., 240 min. and 300 min. of incubation. Additionally, spore growth, as indicated by a color change from colorless to red was determined visually after 24 and 168 hours of incubation. The results are reported in Table VI.

incubation. The enzyme was completely inactivated after 120 minutes of ethylene oxide exposure, demonstrating that 120 minutes of ethylene oxide exposure is a complete and efficacious sterilization cycle. Some residual enzyme activity was detected after 3 and 4 hours of incubation in marginal sterilization cycles of 30 and 60 minutes.

EXAMPLE 7

*Bacillus stearothermophilus* spores ("ATCC 7953"), obtained as described in Example 1, were suspended in distilled water, after one wash, at a population of $1 \times 10^8$ spores/ml. The following procedure was used to purify the enzyme alpha-D-glucosidase. The suspension (200 ml) was dialyzed against 2 l of a solution of 10 mM acetate buffer and 5 mM $CaCl_2$, pH 6.2, overnight at 4° C. Insoluble residues were then removed by centrifugation. The supernatant was fractionated with solid ammonium sulfate. The precipitates from 20%-60% ammonium sulfate were collected on a Buchner funnel containing a filter pad. The filter pad was prepared by passing a suspension (100 g/l) of "Celite ® Filter Aid", commercially available from Manville Specialty Product Group, Lompoc, Calif. over two sheets of Whatman No. 1 filter paper. After filtration, the "Celite ® Filter Aid" pad was suspended in 20 ml of the solution of 10 mM acetate buffer and 5 mM CaCl2, pH 6.2, and stirred for 4 hours at 4° C. "Celite ® Filter Aid" was removed from the soluble enzyme by filtration. The light brown enzyme solution was dialyzed overnight against 4 L of the solution of 10 mM acetate buffer and 5 mM $CaCl_2$ at 4° C. The dialyzed solution was removed from the dialysis tubing and filtered to remove insoluble debris.

The dialyzed solution was adjusted to pH 6.2 and two volumes of cold acetone ($-20°$ C.) were added with stirring. The acetone-enzyme solution was held at $-20°$ C. for 6 hours. The light brown precipitate was collected by gravity filtration at 4° C. and dissolved in 10 ml of the solution of 10 mM acetate buffer and 5 mM $CaCl_2$, pH 6.2. The light amber solution was adjusted to pH 5.5 by the addition of 0.1M acetate buffer, pH 4.6. The solution was again treated with two volumes of cold acetone ($-20°$ C.) and stored at 20° C. overnight. The precipitate was collected by gravity filtration and dissolved in 10 ml of the solution of 10 mM acetate buffer and 5 mM $CaCl_2$, pH 6.2. The light amber solution was dialyzed for 48 hours against 4 L of a solution of 50 mM phosphate buffer and 5 mM EDTA, pH 6.2 (Buffer A), at 4° C. with complete buffer change every 24 hours.

Five ml of the dialyzed sample was loaded in a col-

TABLE VI

| Ethylene Oxide Exposure | FLUORESCENCE Incubation Time (minutes) at 37° C. Number of positives/3 tested | | | | | | | Spore Growth | |
|---|---|---|---|---|---|---|---|---|---|
| | 30 | 60 | 90 | 120 | 180 | 240 | 300 | 24 hr. | 168 hr. |
| 0 | 3 | 3 | 3 | 3 | 3 | 3 | 3 | 3 | 3 |
| 15 | 0 | 0 | 3 | 3 | 3 | 3 | 3 | 3 | 3 |
| 30 | 0 | 0 | 0 | 0 | 3* | 3* | 3* | 0 | 0 |
| 60 | 0 | 0 | 0 | 0 | 0 | 3* | 3* | 0 | 0 |
| 120 | 0 | 0 | 0 | 0 | 0 | 0 | 0 | 0 | 0 |

*Indicates one or more false positive reactions which appear to be the result of residual enzyme activity following spore inactivation in marginal sterilization cycles.

Table VI illustrates that in the devices where the spore survived the 15 minute ethylene oxide exposure, the fluorescence that resulted from the reaction of active β-D-glucosidase with the 4-methylumbelliferyl-B-D-glucoside was visually detected after 90 minutes of umn ($2.5 \times 30$ cm) packed with "DEAE-Sephadex ® Beads", commercially available from Pharmacia, Inc., Piscataway, N.J., and equilibrated with 50 mM phosphate buffer and 5 mM EDTA, pH 6.2. The column was washed successively with: a) 500 ml of Buffer A, and b) 200 ml of a linear 0–0.8M NaCl gradient in Buffer A. The flow rate was kept at approximately 5 ml/60 min. The active fractions that appeared were collected and dialyzed for 48 hours against 4 L of distilled water, with a complete change after 24 hours. The lyopholized fractions were suspended in a 3 ml of a solution of 150 mM phosphate buffer and 5 mM EDTA, pH 6.2 (Buffer B). This suspension was passed through a column (2.5×30 cm) packed with "Sephadex ® G-100 Beads", commercially available from Pharmacia, Inc. with Buffer B at an approximate flow rate of 5 ml/60 min. The active fractions were collected and dialyzed against 4 L of distilled water. The dialyzed fractions were then lyopholized.

Seven 6.35×28.58 ($\frac{1}{4}\times\frac{9}{8}$ inch) strips of "S&S 903 Grade Filter Paper" were saturated with a suspension of 0.02M purified alpha-D-glucosidase in distilled water. Seven other paper strips, of the same type and dimension, were saturated with a $1\times10^6$ spores/ml solution of $B.$ $stearothermophilus$ spores, ("ATCC 7953"), obtained as described in Example 1, suspended in distilled water. All carrier strips were air dried overnight at ambient temperature (20° C.).

Devices were assembled using these spore strips as shown in FIGS. 1 and 2, and described in Example 1 as Device 1. These devices were exposed in a gravity displacement steam sterilizer, commercially available as an "Amsco Eagle TM Model 2013 Sterilizer" at 132° C. and 469.4 kg/cm$^2$ (33 psi) for 0.5, 1.0, 1.5, 2.0, 2.5 and 3.0 minutes. After exposure the inner ampoules containing the enzyme substrate and nutrient medium were crushed and the units were incubated at 56° C. for 24 hours. An ultraviolet light ($\lambda=366$ nm) was used to illuminate the vials for visually read fluorescence.

Relative fluorescence of each device was also measured using a 3M FluoroFAST TM 96 Fluorometer", at 366 nm. The results are recorded in Table VII.

TABLE VII

| Exposure Time (min) | FLUORESCENCE | | | |
|---|---|---|---|---|
| | Device with purified enzyme | | Device with spore strip | |
| | Observed[1] | Fluorometer (RFU) | Observed[1] | Fluorometer (RFU) |
| 0.0 | + | 3954 | + | 3182 |
| 0.5 | + | 1421 | + | 1876 |
| 1.0 | + | 860 | + | 1350 |
| 1.5 | + | 513 | + | 830 |
| 2.0 | + | 456 | + | 636 |
| 2.5 | − | 367 | − | 357 |
| 3.0 | − | 322 | − | 312 |

[1]"+" indicates fluorescence by visual observation while "−" indicates no fluorescence by visual observance.

The results in Table VII illustrate that the devices which employ the purified enzyme had the same visually observed fluorescence, and approximately the same measured fluorescence, as the devices employing $B.$ $stearothermophilus$. Thus, this example illustrates that activity of the purified enzyme alone, not bound to the spore from which it is derived, is useful to detect spore survival.

What is claimed is:

1. A unitary sterility indicator comprising:
   a) an outer container having liquid impermeable and substantially gas non-absorptive walls, said container having at least one opening therein;
   b) gas-transmissive, bacteria-impermeable means covering said at least one opening;
   c) contained within said outer container a source of active enzyme which provides a detectable amount of said enzyme, said enzyme having sufficient activity following a sterilization cycle which is sublethal to at least one test microorganism commonly used to monitor sterilization, to react with an effective amount of a substrate system for said enzyme to produce a detectable enzyme-modified product within less than twenty-four hours, yet said enzyme having activity which is reduced to "background" following a sterilization cycle which is lethal to said test microorganism;
   d) a sealed, openable gas and liquid impermeable inner container, containing an aqueous reaction medium capable of permitting said active enzyme to react with a substrate system for said enzyme, said inner container being disposed in said outer container and said inner container, when opened, permitting said aqueous reaction medium to contact said source of active enzyme;
   e) an enzyme substrate system contained in at least one of said containers and capable of reacting in the presence of said aqueous reaction medium with an active enzyme surviving said sublethal sterilization cycle to produce a detectable enzyme-modified product; and
   f) means contained within said outer container for restricting the volume in which the enzyme-modified product is contained, after said inner container is opened and said medium is allowed to contact said source of active enzyme, to a volume which is less than the volume of said aqueous reaction medium contained in said inner container.

2. The indicator of claim 1, wherein said means of restriction comprises a nonwoven web placed within said outer container and shaped such that it separates at least a major portion of said active enzyme from said inner container.

3. The indicator of claim 2 wherein said nonwoven web is comprised of fibers selected from the group consisting of cotton, rayon, polypropylene, nylon and glass.

4. The indicator of claim 1, wherein said means of restriction comprises carrying said source of active enzyme of a wick strip, said wick strip being comprised of a water-absorbent material, and said wick strip being of a size and carrying said source of active enzyme in such a position that when said inner container is opened, the aqueous reaction medium contained therein is in contact with that portion of the wick strip which does not carry said source of active enzyme.

5. The indicator of claim 4, wherein said wick strip comprises a material selected from the group consisting of filter paper, cloth and rayon.

6. The indicator of claim 1, wherein said source of active enzyme is bacteria or fungus, in either the spore or vegetative state.

7. The indicator of claim 1, wherein said source of active enzyme is isolated enzyme derived from a microorganism.

8. The indicator of claim 1, wherein said active enzyme is one which:
   a) when subjected to a sterilization cycle which would be sufficient to decrease the population of $1\times10^6$ test microorganisms to zero, as measured by outgrowth of said microorganisms, has activity equal to "background", as measured by reaction with an effective amount of an enzyme substrate system capable of reacting with said active enzyme to produce a detectable enzyme-modified product; and b) when subjected to a sterilization cycle sufficient to decrease the population of $1 \times 10^6$ of said test microorganisms by at least about 1 log, but less than about 6 logs, has activity greater than said background, as measured by reaction with an effective amount of said enzyme substrate system.

9. The indicator of claim 1, wherein said enzyme is beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, alpha-L-arabinofuranosidase, beta-D-glucuronidase, N-acetyl-$\beta$-glucosaminidase, beta-D-cellobiosidase, alanine aminopeptidase, proline aminopeptidase, tyrosine aminopeptidase, leucine aminopeptidase, phenylalanine aminopeptidase, and fatty acid esterase, which enzyme is derived from spore-forming microorganisms.

10. A unitary sterility indicator comprising:
   a) an outer container having liquid impermeable and substantially gas non-absorptive walls, said container having at least one opening therein;
   b) gas-transmissive, bacteria-impermeable means covering said at least one opening;
   c) contained within said outer container a detectable amount of a microorganism selected from the group consisting of *Bacillus stearothermophilus* and *Bacillus subtilis*;
   d) a sealed, openable gas and liquid impermeable inner container containing a composition consisting of
      1) aqueous nutrient medium capable, with incubation, of promoting growth of said viable microorganisms;
      2) an enzyme substrate capable of reacting in the presence of an aqueous medium with an active enzyme surviving a sublethal sterilization cycle to produce a detectable enzyme-modified product; and
      3) a detector material capable of undergoing a visible color change in response to growth of said microorganism; said inner container being disposed in said outer container and said inner container, when opened, permitting said composition to contact said microorganism; and
   e) means contained within said outer container for restricting the a volume in which said composition and said microorganism are contained together, after said inner container is opened and said composition is allowed to contact said microorganisms, to a volume which is less than the volume of said composition contained in said inner container.

11. A method for testing the efficacy of a sterilization cycle comprising the sequential steps of:

a) subjecting to said sterilization cycle a unitary sterility indicator comprising:
   1) an outer container having liquid impermeable and substantially gas non-absorptive walls, said container having at least one opening therein;
   2) gas-transmissive, bacteria-impermeable means covering said at least one opening;
   3) contained within said outer container a source of active enzyme which provides a detectable amount of said enzyme, said enzyme having sufficient activity following a sterilization cycle which is sublethal to at least one test microorganism commonly used to monitor sterilization, to react with an effective amount of a substrate system for said enzyme to produce a detectable enzyme-modified product within less than twenty-four hours, yet said enzyme having activity which is reduced to "background" following a sterilization cycle which is lethal to said test microorganism;
   4) a sealed, openable gas and liquid impermeable inner container, containing an aqueous reaction medium capable of permitting said active enzyme to react with a substrate for said enzyme, said inner container being disposed in said outer container and said inner container, when opened permitting said aqueous reaction medium to contact said source of active enzyme;
   5) an enzyme substrate contained in at least one of said containers, and capable of reacting in the presence of said aqueous reaction medium with an active enzyme surviving said sublethal sterilization cycle to produce a detectable enzyme-modified product; and
   6) means contained within said outer container for restricting the volume in which said enzyme-modified product is contained, after said inner container is opened and said medium is allowed to contact said source of active enzyme, to a volume which is less than the volume of said aqueous reaction medium contained in said inner container;

b) causing said openable inner container inside said outer container to open, after said sterilization cycle, permitting said aqueous rection medium to contact any residual active enzyme and said enzyme substrate; and c) incubating said indicator under conditions sufficient to promote reaction of any enzyme remaining active after said sterilization cycle with said enzyme substrate.

12. The indicator of claim 2, wherein said enzyme substrate system reacts with an active enzyme surviving said sublethal sterilization cycle to produce a detectable enzyme-modified product within less than eight hours.

13. The indicator of claim 2, wherein said enzyme substrate system reacts with an active enzyme surviving said sublethal sterilization cycle to produce a detectable enzyme-modified product within less than three hours.

* * * * *

UNITED STATES PATENT AND TRADEMARK OFFICE
CERTIFICATE OF CORRECTION

PATENT NO. : 5,223,401
DATED : June 29, 1993
INVENTOR(S) : William E. Foltz, Richard R. Matner, & Lewis P. Woodson It is certified that error appears in the above-indentified patent and that said Letters Patent is hereby corrected as shown below:

Col. 10, Line 14, "4-methylumbelliferyl-a-D-glucoside" should read --4-methylumbelliferyl-$\beta$-D-glucoside--.

Col. 19, Line 23, Footnote of Table I, first line "on" should read --one--.

Col. 21, Line 53, Footnote of Table III, first line "on" should read --one--.

Signed and Sealed this

Tenth Day of January, 1995

Attest:

BRUCE LEHMAN

Attesting Officer

Commissioner of Patents and Trademarks